(12) United States Patent
Miller

(10) Patent No.: US 8,216,550 B2
(45) Date of Patent: *Jul. 10, 2012

(54) LUCIFERINS

(75) Inventor: Stephen C. Miller, Cambridge, MA (US)

(73) Assignee: University of Massachusetts, Shrewsbury, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/027,233

(22) Filed: Feb. 14, 2011

(65) Prior Publication Data

US 2011/0136156 A1    Jun. 9, 2011

Related U.S. Application Data

(62) Division of application No. 12/040,812, filed on Feb. 29, 2008, now Pat. No. 7,910,087.

(60) Provisional application No. 60/904,731, filed on Mar. 2, 2007.

(51) Int. Cl.
*G01N 33/53* (2006.01)
*C12Q 1/66* (2006.01)
*C12N 9/02* (2006.01)

(52) U.S. Cl. .............. 424/9.1; 435/8; 435/189

(58) Field of Classification Search .............. 435/8, 189; 424/9.1
See application file for complete search history.

(56) References Cited

U.S. PATENT DOCUMENTS

| | | | |
|---|---|---|---|
| 5,149,807 A | 9/1992 | Hammond et al. | |
| 5,932,474 A | 8/1999 | Tsien et al. | |
| 6,008,378 A | 12/1999 | Tsien et al. | |
| 6,054,271 A | 4/2000 | Tsien et al. | |
| 6,451,569 B1 | 9/2002 | Tsien et al. | |
| 6,495,355 B1 | 12/2002 | Contag et al. | |
| 6,686,458 B2 | 2/2004 | Tsien et al. | |
| 6,737,245 B1 | 5/2004 | Francis et al. | |
| 6,825,355 B2 | 11/2004 | Das et al. | |
| 7,524,876 B2 | 4/2009 | Takakura et al. | |
| 7,910,087 B2 * | 3/2011 | Miller | 424/9.1 |
| 2003/0083373 A1 | 5/2003 | Tsien et al. | |
| 2003/0087328 A1 | 5/2003 | Pollok et al. | |
| 2003/0157519 A1 | 8/2003 | Zhang et al. | |
| 2003/0166905 A1 | 9/2003 | Wood et al. | |
| 2003/0203404 A1 | 10/2003 | Joly | |
| 2003/0224421 A1 | 12/2003 | Herrmann et al. | |
| 2004/0214227 A1 | 10/2004 | Joly | |
| 2005/0026171 A1 | 2/2005 | Hawkins et al. | |
| 2005/0131217 A1 | 6/2005 | Tsien et al. | |
| 2005/0136449 A1 | 6/2005 | Hanson et al. | |
| 2005/0176065 A1 | 8/2005 | Hanson | |
| 2005/0239135 A1 | 10/2005 | Bogoev et al. | |
| 2005/0272114 A1 | 12/2005 | Darzins et al. | |
| 2006/0073529 A1 | 4/2006 | Contag et al. | |
| 2006/0099679 A1 | 5/2006 | Tsien et al. | |
| 2007/0015790 A1 | 1/2007 | Cali et al. | |
| 2008/0299592 A1 | 12/2008 | Miller | |

FOREIGN PATENT DOCUMENTS

| | | |
|---|---|---|
| AU | 768176 B | 9/2000 |
| AU | 779263 B | 4/2001 |
| EP | 1088233 | 4/2001 |
| JP | 2001224398 | 8/2001 |
| WO | WO99/21013 | 4/1999 |
| WO | WO00/49171 | 8/2000 |
| WO | WO01/18195 | 3/2001 |
| WO | WO03/033650 | 4/2003 |
| WO | WO2004/034054 | 4/2004 |
| WO | WO2004/059294 | 7/2004 |
| WO | WO2005/033286 | 4/2005 |
| WO | WO2005/038029 | 4/2005 |
| WO | WO2005/040197 | 5/2005 |
| WO | WO2005/054427 | 6/2005 |
| WO | WO2006/093529 | 9/2006 |

OTHER PUBLICATIONS

Adams et al., "New biarsenical ligands and tetracysteine motifs for protein labeling in vitro and in vivo: synthesis and biological," J. Am. Chem. Soc. 124:6063-76 (2002).
Arai et al., "Detection of protein-protein interaction by bioluminescence resonance energy transfer from firefly luciferase to red fluorescent protein," J. Biosci. Bioeng. 94:362-364 (2002).
Branchini et al., "Red- and green-emitting firefly luciferase mutants for bioluminescent reporter applications," Anal. Biochem. 345(1):140 (2005).
Contag et al., "Advances in vivo bioluminescence imaging of gene expression," Annu. Rev. Biomed. Eng. 4:235-620 (2002).
Griffin, B. A. et al., "Specific covalent labeling of recombinant protein molecules inside live cells," Science 281: 269-272 (1998).
Gurskaya et al., "GFP-like chromoproteins as a source of far-red fluorescent proteins," FEBS Lett. 507(1) :16-20 (2001).
Martin et al., "Mammalian cell-based optimization of the biarsenical-binding tetracysteine motif for improved fluorescene and affinity," Nat. Biotechnol. 23 :1308-14 (2005).
Nakanishi et al., "Imaging of conformational changes of proteins with a new environment-sensitive fluorescent probe designed for site-specific labeling of recombinant proteins in live cells," Anal. Chem. 73:2920-28 (2001.)
Rice et al., "In vivo imaging of light-emitting probes," Journal of Biomedical Optics 6:432-440 (2001). Shaner et al., "Improved monomeric red, orange and yellow fluorescent proteins derived from Discosoma sp. red fluorescent protein," Nat. Biotechnol. 22 :1567-1572 (2004).
So et al., "Self-illuminating quantum dot conjugates for in vivo imaging," Nat. Biotechnol. 24(3):339-43 (2006).
Tirat et al., "Evaluation of two novel tag-based labeling technologies for site-specific modification of proteins," Int. J. Biol. Macromol. 39 :66-76 (2006).
Viviani et al., "Cloning, sequence analysis, and expression of active Phrixothrix railroad-worms luciferases: relationship between bioluminescence spectra and primary structures," Biochemistry 38:8271-79 (1999).

(Continued)

*Primary Examiner* — Kamal Saeed
*Assistant Examiner* — Kristin Bianchi
(74) *Attorney, Agent, or Firm* — Fish & Richardson P.C.

(57) ABSTRACT

Novel luciferins, methods of making luciferins, and uses of the same are disclosed.

16 Claims, 13 Drawing Sheets

OTHER PUBLICATIONS

Viviani et al., "The influence of Ala243 (Gly247), Arg215 and Thr226 (Asn230) on the bioluminescence spectra and pH-sensitivity of railroad worm, check beetle and firefly luciferases," Photochem. Photobiol. 76 :538-44 (2002).

Wang et al., "Renilla luciferase-Aequorea GFP (Ruc-GFP) fusion protein, a novel dual reporter for real-time imaging of gene expression cell cultures and in live animals," Mol. Genet. Genomics 268 :160-168 (2002).

Weissleder et al., "Shedding light onto live molecular targets," Nat. Med. 9(1):123-8 (2003).

White et al., "Amino analogs of firefly luciferin and biological activity thereof," J. Am. Chem. Soc. 88:2015 (1966).

Xu, Y. et al., "A bioluminescence resonance energy transfer (BRET) system: Application to interacting circadian clock proteins," Proc. Natl. Acad. Sci. USA 96: 151-156 (1999).

Xu et al., "Bioluminescence resonance energy transfer: monitoring protein-protein interactions in living cells," Methods Enzymol. 360 :289-301 (2003).

Yamakawa et al., "Rapid homogeneous immunoassay of peptides based on bioluminescence resonance energy transfer from firefly luciferase," J. Biosci. Bioeng. 93 :537-542 (2002).

* cited by examiner

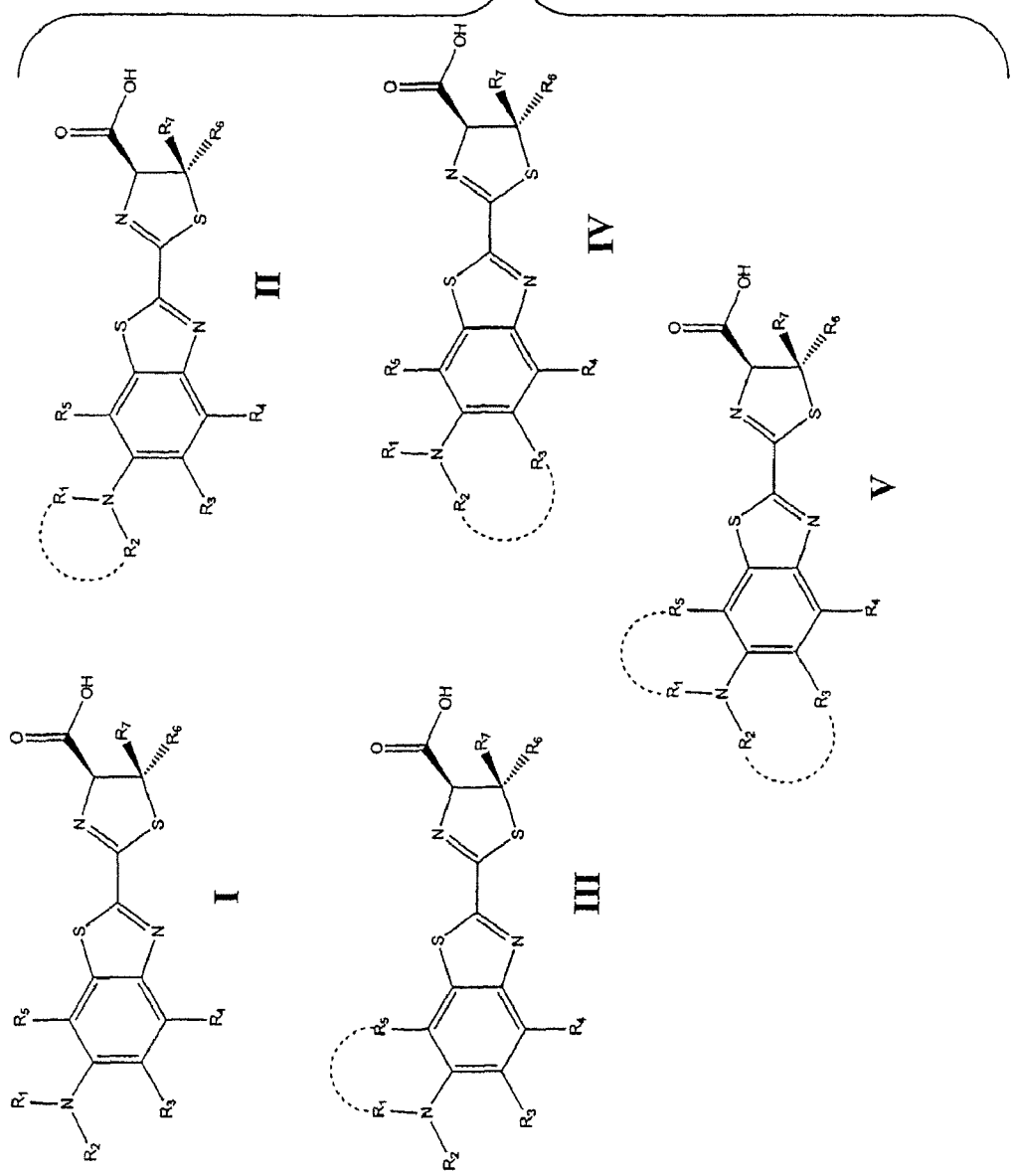

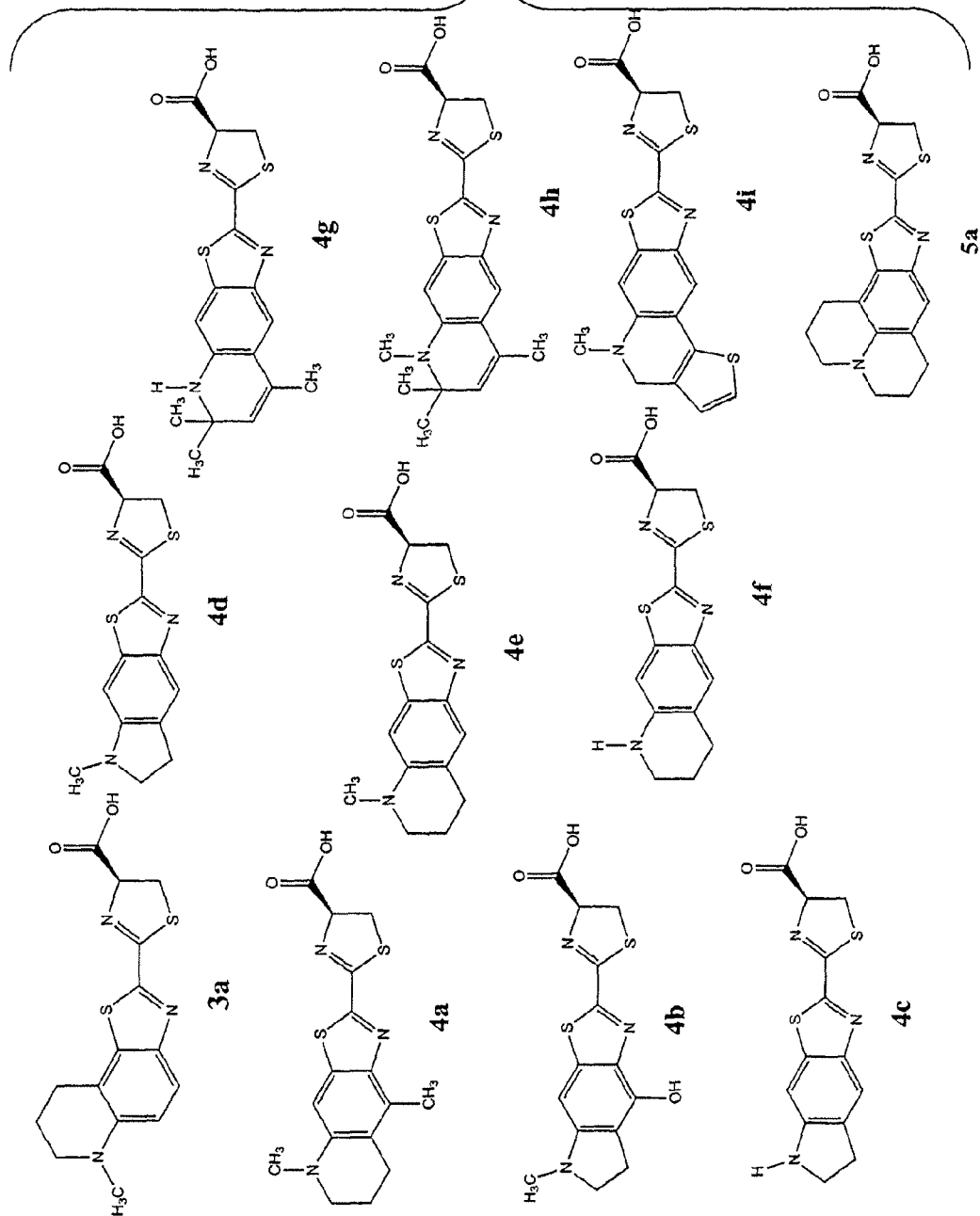

NIR fluorophore can be at positions 1, 2 or 3

LUCIFERINS

CLAIM OF PRIORITY

This application is a divisional of U.S. patent application Ser. No. 12/040,812, filed on Feb. 29, 2008, now U.S. Pat. No. 7,910,087 which claims the benefit of U.S. patent application Ser. No. 60/904,731, filed on Mar. 2, 2007. The entire contents of the foregoing are hereby incorporated by reference.

TECHNICAL FIELD

This invention relates to luciferins, methods of making luciferins, and to uses of the same.

BACKGROUND

Firefly luciferase is widely used for bioluminescent imaging in mice. However, when combined with firefly luciferin, the emitted yellow-green light (560 nm) penetrates poorly through tissue due to absorption by hemoglobin and Rayleigh scattering. For optimal bioluminescent imaging, longer wavelengths (>650 nm) would be desirable.

Some mutants of firefly and click beetle luciferases maximally emit light as high as 615 nm (Anal. Biochem., 2005, 345(1):140), and railroad worm luciferase naturally emits light at 623 nm (Biochemistry, 1999, 38(26):8271). Most of these red-shifted luciferases, however, have not been well characterized, and for those examples that have, the bathochromatic shift in emission is concomitant with a substantial loss in light output, and often a significant loss of affinity for both luciferin and ATP.

Referring to FIG. 1, enzymatic oxidation of firefly luciferin (1) with firefly luciferase (LUC), and subsequent decarboxylation, generates oxyluciferin (described by (1'A) and (1'B)) in an electronically-excited state (FIG. 1). This molecule returns to the electronic ground state by emitting a photon with very high quantum yield (0.9) (see, e.g., Arch. Biochem. Biophys., 88 (1960) 136-141). The wavelength of the emitted photon is determined by the structure and electronic properties of the oxyluciferin chromophore within the luciferase binding pocket. At physiological pH, the emission wavelength of wild-type firefly luciferase is 560 nm. At low pH (~6), this emission is red-shifted to as high as 617 nm, but with a decreased quantum yield.

SUMMARY

Generally, luciferins, e.g., N-substituted amino luciferins, such as N-alkylamino luciferins, or salts or derivatives thereof are disclosed, as well as methods of use thereof. These new luciferins are substrates for luciferases, i.e., they emit light when combined with a luciferase.

In one aspect, the invention features compounds of Structure (I), or salts or acid esters thereof.

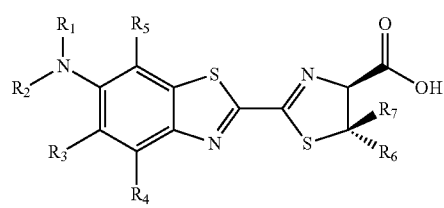

In Structure (I), $R_1$ and $R_2$ are each independently H (provided that $R_1$ and $R_2$ are not both H), a first moiety including up to 12 carbon atoms, or a first moiety including a near infrared fluorophore. $R_3$ is H, OH, a second moiety including up to 12 carbon atoms, or a second moiety that includes a near infrared fluorophore. $R_4$ and $R_5$ are each independently H, OH, or a moiety that includes up to 6 carbon atoms. $R_6$ and $R_7$ are each independently H, or a moiety including up to 8 carbon atoms. $R_1$, $R_2$, $R_3$, or $R_5$ may together with one or more of its immediate neighbors define one or more ring systems, each including up to 14 carbon atoms.

In some embodiments, the first and/or second moiety including up to 12 carbon atoms also includes one or more N, O, P, S, F, Cl, Br, or I.

The moieties that include up to 6 carbon atoms and/or the moieties that include up to 8 carbon atoms can also include one or more N, O, P, S, F, Cl, Br, or I.

The first and/or second moieties that include the near infrared fluorophore can also include a spacer including up to 24 carbon atoms, or a polymer fragment, e.g., a polymer fragment of a water-soluble polymer such as a polyethylene glycol or a copolymer thereof. The spacer can also include one or more N, O, P, S, F, Cl, Br, or I.

For example, the one or more defined ring systems can further include one or more N, O, P, S, F, Cl, Br, or I.

In particular embodiments, $R_3$, $R_4$, $R_5$, $R_6$, and $R_7$ are each hydrogen, or an alkyl group, e.g., one having fewer than 6 carbon atoms, or having fewer than 4 carbon atoms.

In some embodiments, $R_1$ and $R_2$ together define a ring, the compounds being represented by Structure (II), which is shown below.

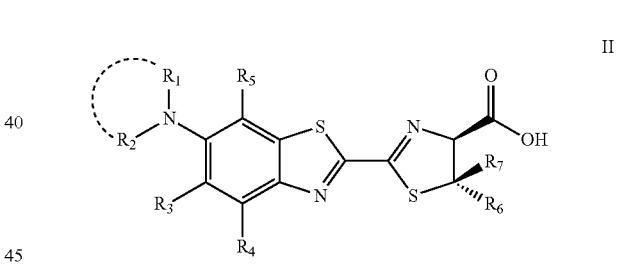

In some embodiments, $R_1$ and $R_5$ together define a ring, the compounds being represented by Structure (III). Such compounds are characterized as having hindered rotation about the Ar—N($R_1R_2$) bond of the of Structure (III). Rotation can be further hindered, e.g., by having a carbon-carbon double bond in the ring. A double bond may also provide additional conjugation with the π-system of the chromophore.

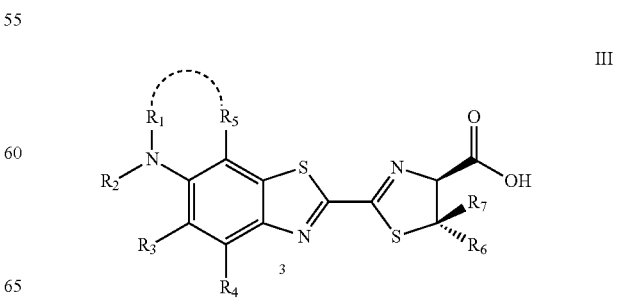

In other embodiments, $R_2$ and $R_3$ together define a ring, the compounds being represented by Structure (IV). Such compounds are characterized as having hindered rotation about the Ar—$N(R_1R_2)$ bond of the of Structure (IV).

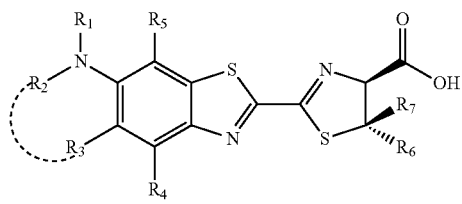

IV

In certain embodiments, $R_1$ and $R_5$ and $R_2$ and $R_3$ together define a ring, the compounds being represented by Structure (V). Such compounds are characterized as having extremely hindered rotation about the Ar—$N(R_1R_2)$ bond of the of Structure (V). Rotation can be further hindered, e.g., by having one or more carbon-carbon double bonds in one or more rings.

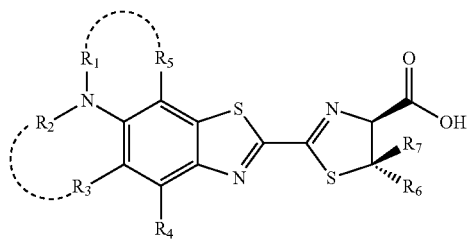

V

In some instances, the one or more ring systems described above can define a 5, 6, and/or 7-membered rings.

In some implementations, $R_1$ and/or $R_2$ and/or $R_3$ comprise a near infrared fluorophore.

In specific implementations, the compounds of Structure (I) are represented by Structure (VII).

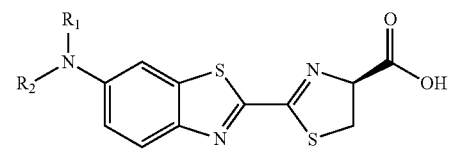

VII

In such instances, $R_1$ and/or $R_2$ can be, e.g., alkyl groups, such as methyl groups.

The salts of any of the luciferins described herein can be, e.g., lithium, sodium, potassium, calcium, magnesium or ammonium salts (e.g., trialkylammonium salts). The esters can be, e.g., NHS esters, alkyl esters (e.g., C1-C3 alkyl esters), phenyl esters, benzyl esters or adenosine monophosphate (AMP) esters.

In another aspect, the invention features N-alkyl luciferins, or salts or acid ester thereof. For example, the N-alkyl luciferin can be a mono-alkyl luciferin or a di-N-alkyl luciferin.

In a specific embodiment, the N-alkyl luciferin has Structure (1a), which is shown below.

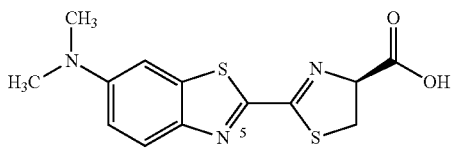

1a

In some embodiments, when $R_1$ is not H, $R_2$ is a substrate for a protease (e.g., an amino acid residue or polypeptide). In some embodiments, the carboxyl group is covalently bound to a protecting group. See, e.g., U.S. Pat. Nos. 5,035,999 and 7,148,030.

In another aspect, the invention features methods of generating light that include providing a luciferase having a binding pocket sized for any luciferin described herein (or an equivalent thereof, e.g., a salt or ester thereof); and combining the luciferin with the luciferase. The luciferase can be a wild-type luciferase, such as a firefly, click beetle, or railroad worm luciferase, or a mutated luciferase.

In another aspect, the invention features methods of imaging living cells or animals, e.g., mammals, or humans, that include providing a cell expressing a luciferase, or an animal having at least one cell expressing a luciferase; administering to the cell or animal any one or more of the luciferins described herein (or an equivalent thereof, e.g., a salt or ester thereof); and detecting emission therefrom.

Aspects and/or embodiments of the invention can have any one of, or combinations of, any of the following advantages. Relative to oxyluciferin, the luciferins described herein emit red-shifted light when combined with a suitable luciferase. For example, the luciferins can emit light having a wavelength of greater than 590 nm, e.g., greater than 600 nm, 610 nm, 615 nm, 620, nm, 625 nm, 630 nm, 635 nm, 640 nm, 645 nm, 650 nm, 665 nm, or even greater than 675 nm. Emission from the luciferins can be insensitive to pH. While generally the novel luciferins emit light that is red-shifted relative to oxyluciferin, the precise wavelength emitted can be tuned by selection of the functional groups attached to the luciferin. It is expected that the luciferins described herein will be well tolerated by animals. The luciferins are likely to be more cell permeable than native luciferin, potentially allowing greater access to luciferase within the mouse. Furthermore, the novel luciferins are likely to have a higher affinity for luciferase, which would allow robust light output under conditions where the luciferin is not present at wild-type luciferin saturating concentrations. Modifications in the N-alkyl group(s) could also allow for modulation of wavelength and light output, leading to luciferin substrates with different rates and durations of light output, to best suit the imaging experiment. When luciferins are covalently bonded in a pocket of a luciferase, fluorescent proteins can be provided. In such instances, the chromophore can be protected from the chemical environment in which the fluorescent protein is placed.

"Luciferase" as used herein is an enzyme that operates on a luciferin to produce light, e.g., near-infrared or visible light. The luciferase can be wild-type, or it can be a mutated luciferase. An example of a luciferase is wild-type firefly luciferase. A number of suitable luciferases are known in the art (e.g., Branchini et al., Anal. Biochem. (2005) 345:140-148; Nakatsu et al., Nature (2006) 440:372-376; Viviani et al., Biochemistry (1999) 38:8271).

"Luciferin" as used herein is a material, such as a pure compound or mixture of compounds, that in the presence of a luciferase produces light. An example of a luciferin is firefly luciferin.

"A near infrared fluorophore" as used herein is one having a maximum emission of greater than 600 nm at physiological pH, e.g., 650 nm or above.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference herein in their entirety for all that they contain. In case of conflict, the present specification, including definitions, will control. It is not an admission that any of the information provided herein is prior art or relevant to the presently claimed inventions, or that any publication specifically or implicitly referenced is prior art. In addition, the materials, methods, and examples are illustrative only and not intended to be limiting.

Other features and advantages of the invention will be apparent from the following detailed description, and from the claims.

DESCRIPTION OF DRAWINGS

FIG. 2A is a series of generalized structures for some novel amino luciferins.

FIGS. 2C and 2D are two series of structures for specific novel amino luciferins in which the nitrogen atom of the amino group is a member of one or more rings.

DETAILED DESCRIPTION

Figure 1:
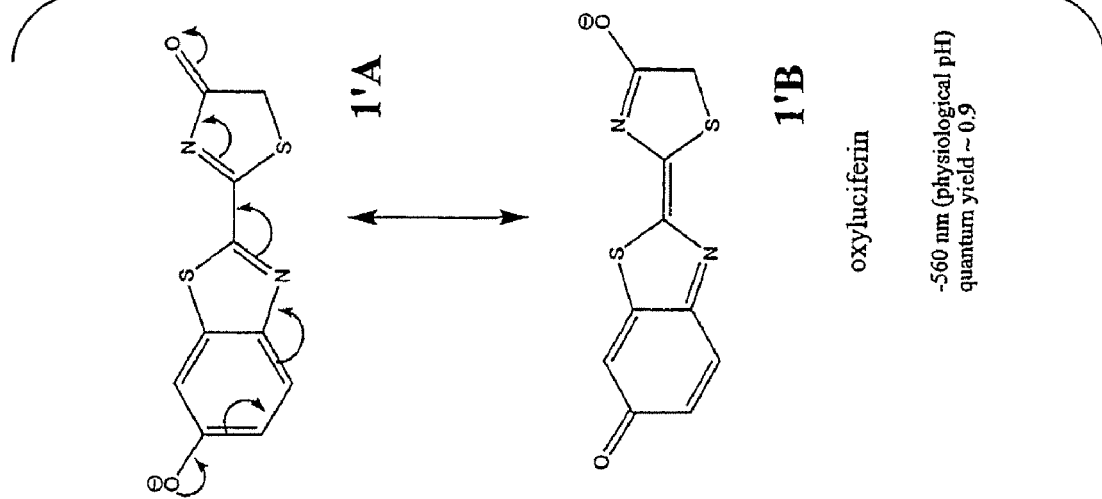
FIG. 1 is a series of structures for firefly luciferin (1) and the corresponding oxyluciferin (represented by (1'A) and (1'B)), that results from enzymatic oxidative decarboxylation with firefly luciferase (LUC).
Figure 1:
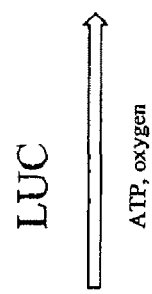
Figure 1:
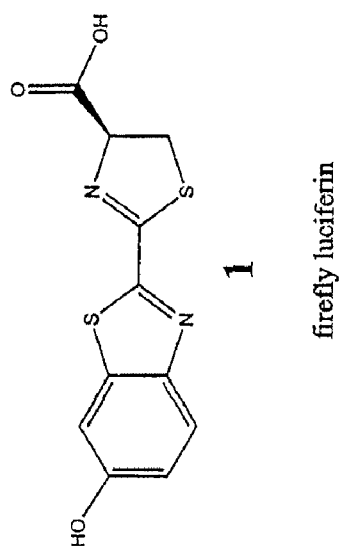

Generally, luciferins, or salts or derivatives thereof, e.g., acid esters thereof, are provided that are sized to fit a binding pocket of a luciferase, such as a wild-type or a mutated luciferase.

Luciferins

Generally, and by reference to FIG. 2A, compounds of Structure (I), or salts or acid esters thereof are provided.

In such compounds of Structure (I), $R_1$ and $R_2$ are each independently H, provided that $R_1$ and $R_2$ are not both H; a first moiety including up to 12 carbon atoms; or a first moiety including a near infrared fluorophore.

The first moiety including up to 12 carbon atoms can also include, e.g., one or more of N, O, P, S, F, Cl, Br, or I. For example, N can be part of an amino group, an amide group or an imine group. For example, O can be part of hydroxyl group, a carboxylic acid group, an ester group, an anhydride group, an aldehyde group, a ketone group or an ether group. For example, S can be part of a thio-ester group, a thiol group or a thio-ether group. For example, P can be part of a phosphate group, a phosphonate group, a phosphine group, or a phosphoramide group.

For example, the first moiety including up to 12 carbon atoms can be or can include a hydrocarbon fragment, e.g., an alkyl group, an alkenyl group, an alkynyl or an aryl group, or a hydrocarbon fragment that is substituted with one or more of N, O, P, S, F, Cl, Br, or I.

The first moiety can also include a near infrared fluorophore, as described herein.

In compounds of Structure (I), $R_3$ is H, OH, a second moiety including up to 12 carbon atoms, or a second moiety including a near infrared fluorophore.

The second moiety including up to 12 carbon atoms can be any of those moieties described above in reference to $R_1$ and $R_2$. The second moiety can also include a near infrared fluorophore, as described herein.

In compounds of Structure (I), $R_4$ and $R_5$ are each independently H; OH; or a moiety including up to 6 carbon atoms. The moiety including up to 6 carbon atoms can also include, e.g., one or more of N, O, P, S, F, Cl, Br, or I. For example, N can be part of an amino group, an amide group, or an imine group. For example, O can be part of hydroxyl group, a carboxylic acid group, an ester group, an anhydride group, an aldehyde group, a ketone group or a ether group. For example, S can be part of a thio-ester group, a thiol group or a thio-ether group. For example, P can be part of a phosphate group, a phosphonate group, a phosphine group, or a phosphoramide group. For example, the moiety including up to 6 carbon atoms can be or can include a hydrocarbon fragment, e.g., an alkyl group, an alkenyl group, an alkynyl or an aryl group, or a hydrocarbon fragment that is substituted with one or more of N, O, P, S, F, Cl, Br, or I.

In compounds of Structure (I), $R_6$ and $R_7$ are each independently H, or a moiety including up to 8 carbon atoms. The moiety including up to 8 carbon atoms can also include, e.g., one or more of N, O, P, S, F, Cl, Br, or I. For example, N can be part of an amino group, an amide group, or an imine group. For example, O can be part of hydroxyl group, a carboxylic acid group, an ester group, an anhydride group, an aldehyde group, a ketone group, or a ether group. For example, S can be part of a thio-ester group, a thiol group, or a thio-ether group. For example, P can be part of a phosphate group, a phosphonate group, a phosphine group, or a phosphoramide group. For example, the moiety including up to 8 carbon atoms can be or can include a hydrocarbon fragment, e.g., an alkyl group, an alkenyl group, an alkynyl or an aryl group, or a hydrocarbon fragment that is substituted with one or more of N, O, P, S, F, Cl, Br, or I.

Figure 2B:
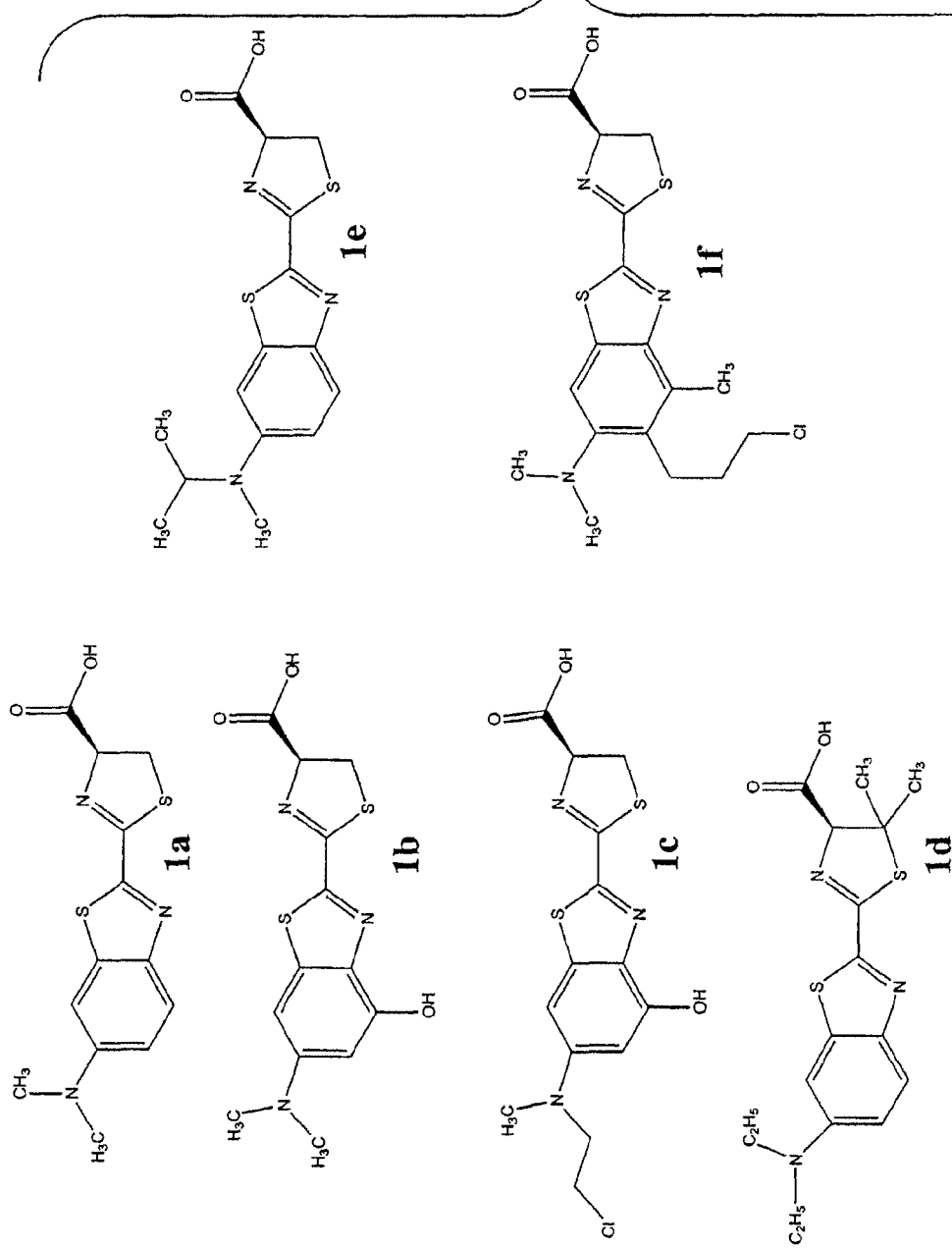
FIG. 2B is a series of structures for specific amino luciferins in which the nitrogen atom of the amino group is not a member of a ring.

Referring now also to FIG. 2B, compounds of Structure (I) in which the amino nitrogen is not a member of a ring are exemplified by Structures (1a), (1b), (1c), (1d), (1e) and (1f). Structure (1c) represents a reactive N-mustard, which can allow for the luciferin to be functionalized with a nucleophile-containing moiety, such as compound bearing an amino or a thiol group. As will be discussed below, such a mustard can allow for, e.g., the covalent bonding of the luciferin in a binding pocket, and can enable, e.g., the preparation of fluorescent proteins.

When the amino nitrogen is not a member of a ring, one or more of $R_1$-$R_7$ can include one or more chiral, or pro-chiral centers.

In compounds of Structure (I), $R_1$, $R_2$, $R_3$, or $R_5$ may together with one or more of its immediate neighbors define one or more ring systems, each including up to 14 carbon atoms. For example, the one or more rings can further include in a ring or substituted on the ring, e.g., one or more of N, O, P, S, F, Cl, Br, or I. For example, the balance of the 14 carbons atoms not in a ring can substitute a ring, e.g., in the form of hydrocarbon fragments, e.g., an alkyl group, an alkenyl group, an alkynyl or an aryl group, or a hydrocarbon fragment that is substituted with one or more of N, O, P, S, F, Cl, Br, or I. For example, N can be part of an amino group, an amide group or an imine group. For example, O can be part of hydroxyl group, a carboxylic acid group, an ester group, an anhydride group, an aldehyde group, a ketone group or a ether group. For example, S can be part of a thio-ester group, a thiol group or a thio-ether group.

In preferred embodiments, the one or more ring systems define one or more 5, 6, and/or 7-membered rings.

Referring back now to FIG. 2A, $R_1$ and $R_2$ can together define a ring such that the compounds are represented by Structure (II).

In desirable embodiments, $R_1$ and $R_5$ can together define a ring such that the compounds are represented by Structure (III). Such compounds are desirable because they have hindered rotation about the Ar—N($R_1R_2$) bond of Structure (III), which can enhance red-shifting.

In other desirable embodiments, $R_2$ and $R_3$ together define a ring such that the compounds are represented by Structure (IV). Such compound are also desired because they have hindered rotation about the Ar—N($R_1R_2$) bond of the of Structure (IV).

In presently preferable embodiments, $R_1$ and $R_5$ and $R_2$ and $R_3$ together define a ring such that the compounds are represented by Structure (V). Such compounds are desirable because they have extremely hindered rotation about the Ar—N($R_1R_2$) bond of the of Structure (V).

When the amino nitrogen forms a member of one or more rings, any such compounds can include one or more chiral, or pro-chiral centers.

Figure 2C:
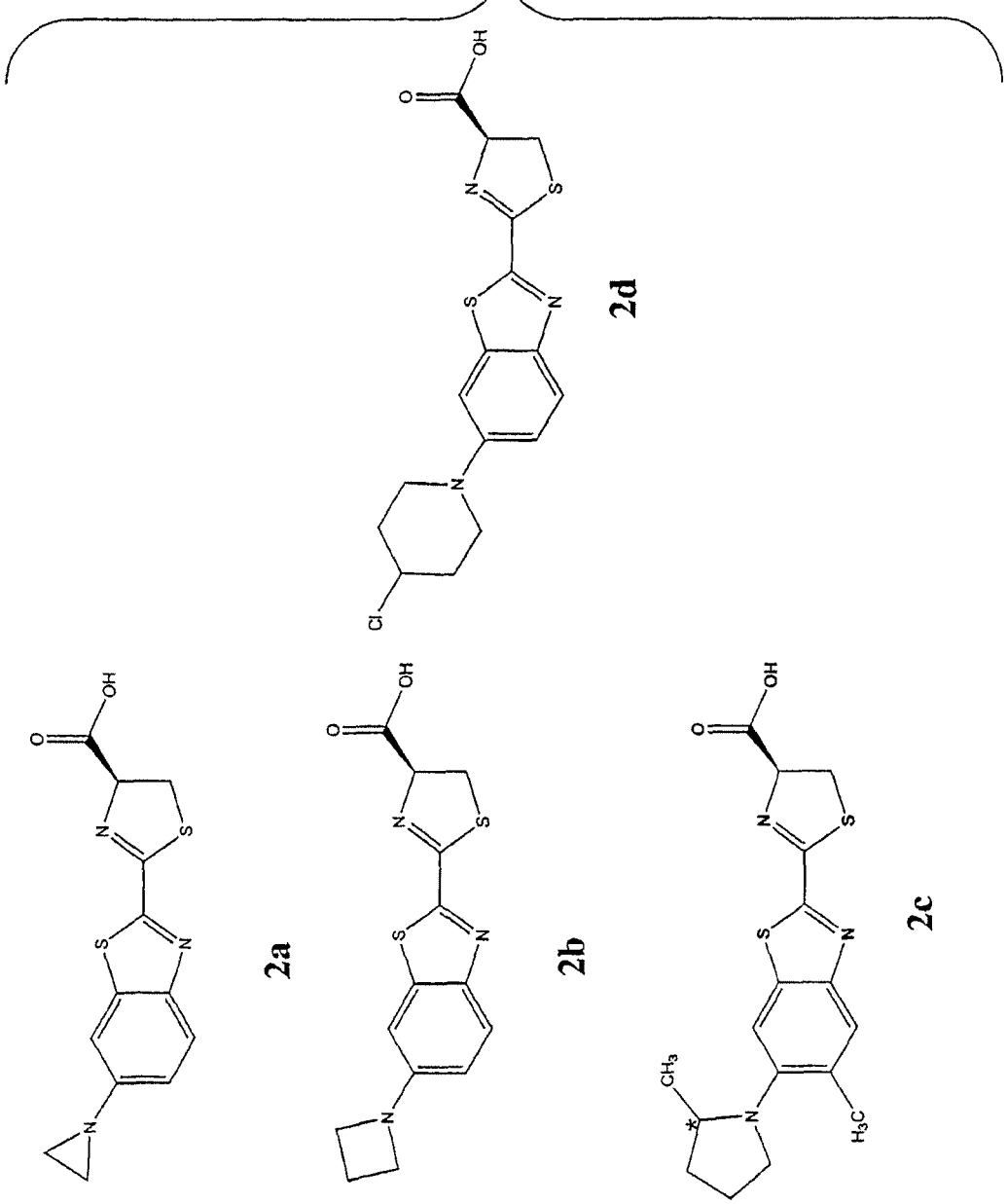

Referring now as well to FIG. 2C, compounds of Structure (I), which are represented by Structure (II) are exemplified in by Structures (2a), (2b), (2c), and (2d). Structure (2c) illustrates a compound having a C-based chiral center (marked with *).

Referring now to FIG. 2D, compounds of Structure (I), which are represented by Structure (III), (IV) and (V) are exemplified by Structures (3a), (4a-4i) and (5a), respectively. Structures (4g-4i), in which the nitrogen atom of the amino group is a member of a 6-membered, unsaturated ring system, and Structure (5a), in which the nitrogen of the amino group is a member of two 6-membered rings, each provide for particularly hindered rotation about the Ar—N($R_1R_2$).

The salts of any of the luciferins described herein can be, e.g., lithium, sodium, potassium, calcium, magnesium or ammonium salts (e.g., trialkylammonium salts). The esters can be, e.g., NHS esters, alkyl esters (e.g., C1-C3 alkyl esters), phenyl esters, benzyl esters or adenosine monophosphate (AMP) esters.

Methods of Making Luciferins

Figure 3A:
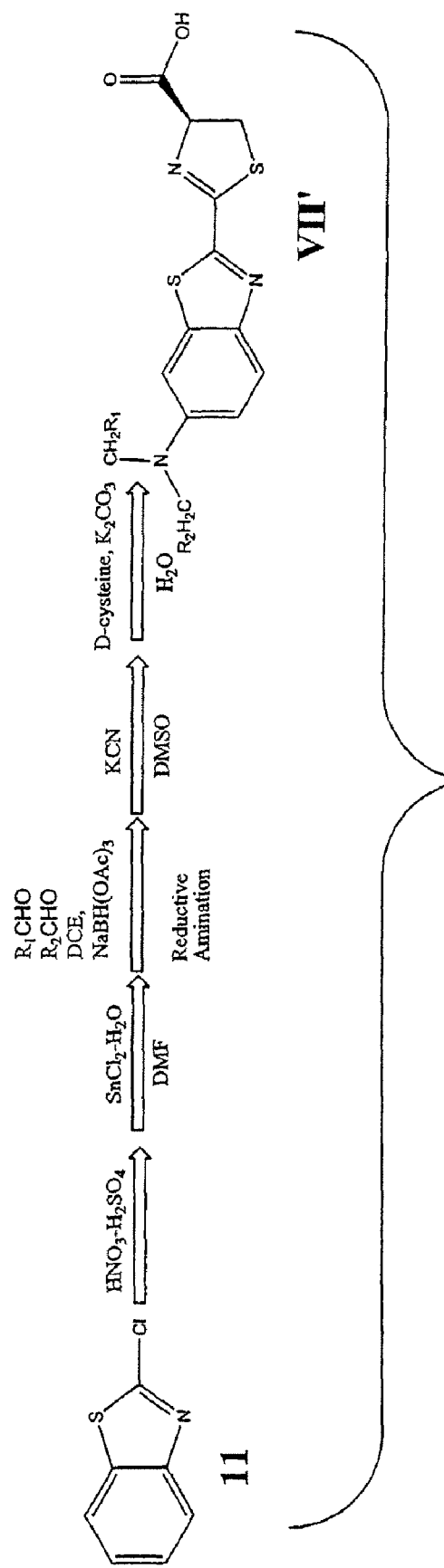
FIGS. 3A-3D are representations of synthetic strategies for making various novel amino luciferins.

Referring now to FIG. 3A, compounds of Structure (VII') can be made from the chlorobenzothiazole (11) by reacting (11) with a mixture of $HNO_3$—$H_2SO_4$ to produce the corresponding nitro compound, which can be reduced to the amine by treatment of the nitro compound with $SnCl_2$—$H_2O$ in DMF. Reductive amination of the amine using $R_1CHO$ and $R_2CHO$ in the presence of DCE and NaBH(OAc)$_3$ (see, e.g., JOC (1996) 61:3849) produces the corresponding substituted amine, and treatment of the substituted amine with KCN in DMSO gives the corresponding nitrile (see, e.g., White et al., JACS (1966) 88:2015). Treatment of the produced nitrile with D-cysteine and $K_2CO_3$ in water produces the desired compounds of Structure (VII'). Alternatively, the Buchwald-Hartwig amination can be used instead of reductive amination (see, e.g., Hartwig, Acc. Chem. Res. (1998), 31, p. 852 and Buchwald et al. Acc. Chem. Res. (1998) 31: 805).

Figure 3B:
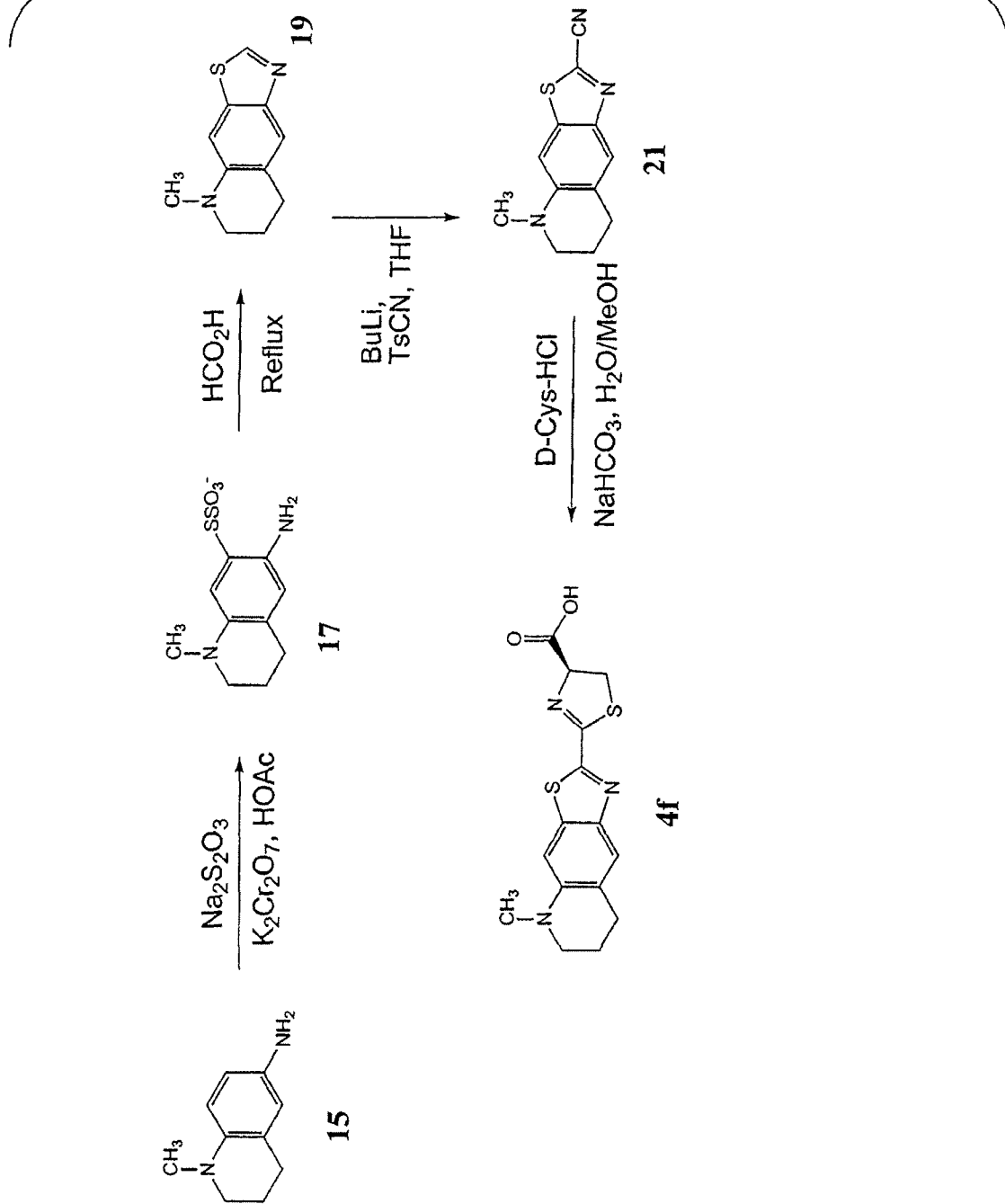
Figure 3C:
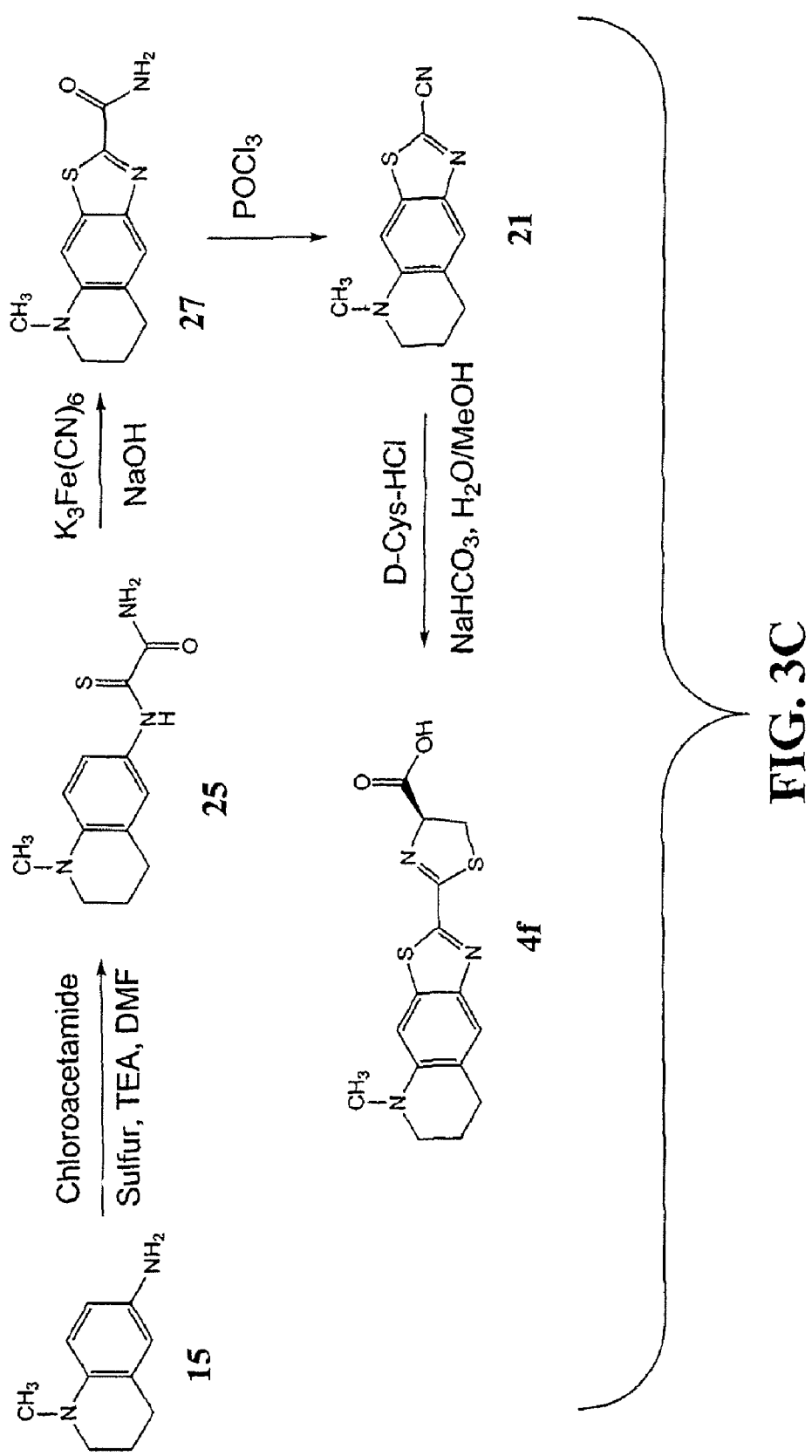
Figure 3D:
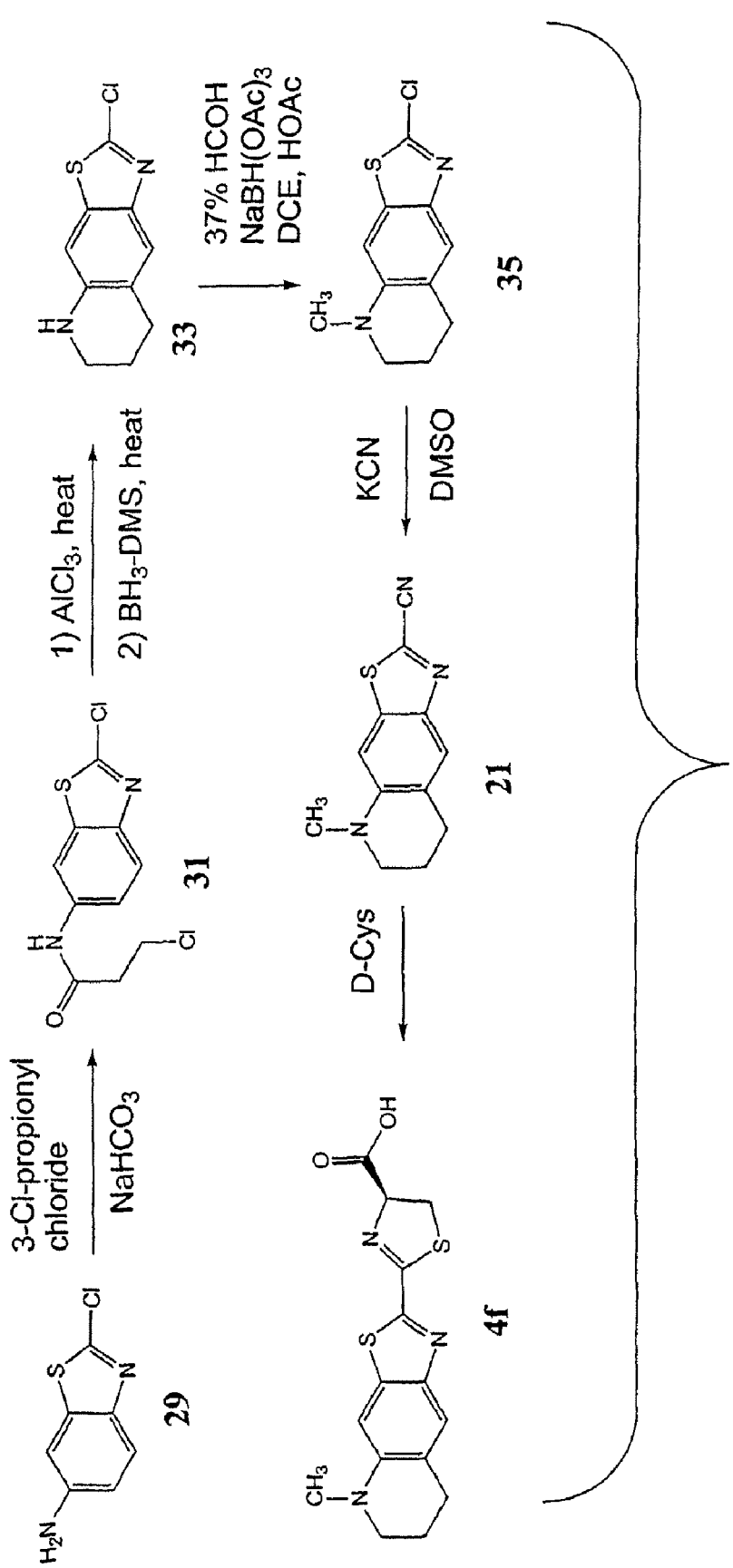

FIGS. 3B-3D show three different methods of making compound (41). FIGS. 3B and 3C show methods that start with 1-methyl-1,2,3,4-tetrahydroquinolin-6-amine (15), while the method shown in FIG. 3D starts with 2-chlorobenzo[d]thiazol-6-amine (29).

Referring now particularly to FIG. 3B, compound (41) is prepared by first treating the hydrochloride salt of compound (15) with sodium thiosulfate and potassium dichromate in acetic acid to give compound (17) (see, e.g., Tetrahedron 60 (2004) 285-289). Treating compound (17) with formic acid under reflux generates benzothiazole derivative (19) (see, e.g., Tetrahedron 60 (2004) 285-289). Treatment of the benzothiazole derivative (19) with butyllithium and then TsCN in THF gives the benzothiazole derivative nitrile (21). Treatment of the benzothiazole derivative nitrile (21) with D-Cys-HCl and NaHCO$_3$ in water/methanol generates compound (41).

Referring now particularly to FIG. 3C, in an alternative synthetic method (Yarovenko et al., Russ. Chem. Bull. Intl., 51:p 144-147 (2002)), compound (41) is prepared by first treating compound (15) with chloroacetamide, sulfur and TEA in DMF, generating compound (25). Treatment of compound (25) with potassium ferricyanide in aqueous sodium hydroxide generates compound (27), which is converted to compound (21) by treatment with POCl$_3$. If desired, potassium ferricyanide in aqueous sodium hydroxide can be replaced by Mn(OAc)$_3$ in acetic acid or bromine in acetic acid. Finally, treatment of the benzothiazole derivative nitrile (21) with D-Cys-HCl and NaHCO$_3$ in water/methanol generates compound (41).

Referring now particularly to FIG. 3D, in another synthetic method, compound (40 is prepared by first treating 2-chlorobenzo[d]thiazol-6-amine (29) with 3-chloro-propionyl chloride and sodium bicarbonate to generate the amide derivative (31). Compound (31) is cyclized by treatment with aluminum chloride, and then the carbonyl is reduced with BH$_3$-DMS, generating compound (33). Treatment of compound (33) with 37% formaldehyde, NaBH(OAc)$_3$, DCE and acetic acid, generates compound (35). The chloro compound (35) is converted into the corresponding nitrile (21) by treatment with KCN in DMSO. Finally, treatment of the benzothiazole derivative nitrile (21) with D-Cys-HCl and NaHCO$_3$ in water/methanol generates compound (40.

Luciferins that Include Fluorophores

As described above, in compounds of Structure (I), $R_1$, $R_2$ and/or $R_3$ can be or can include a fluorophore, e.g., a NIR fluorophore having an a maximum absorption and/or emission of greater than about 600 nm. Such a donor luciferin-acceptor fluorophore configuration can red-shift emission of the donor luciferin by intramolecular BRET to the acceptor fluorophore. BRET is described in "RED-SHIFTED LUCIFERASE", U.S. Provisional Patent Application No. 60/904,582, filed on Mar. 2, 2007, and U.S. patent application Ser. No. 12/040,797 by the same inventor, both of which are incorporated herein by reference in their entirety.

In some embodiments, the acceptor fluorophore has a maximum emission of greater than 605 nm, e.g., greater than 610 nm, 615 nm, 620, nm, 625 nm, 630 nm, 635 nm, 640 nm, 645 nm, 650 nm, 665 nm, or even greater than 675 nm.

In some instances, the fluorophore is directly bonded to the amino group of the luciferin, and in other instances, the fluorophore is further removed by a spacer.

Figure 4A:
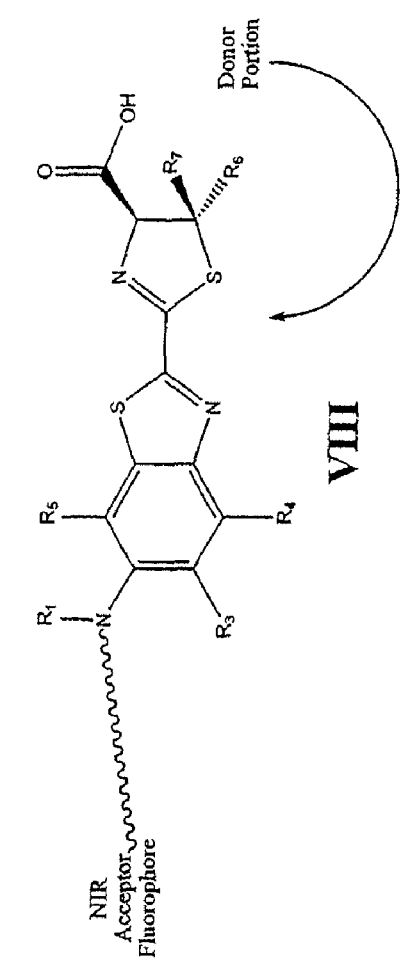
FIG. 4A is a series of generalized structures for novel amino luciferins that include a NIR acceptor fluorophore at positions 1 and 3.
Figure 4A:
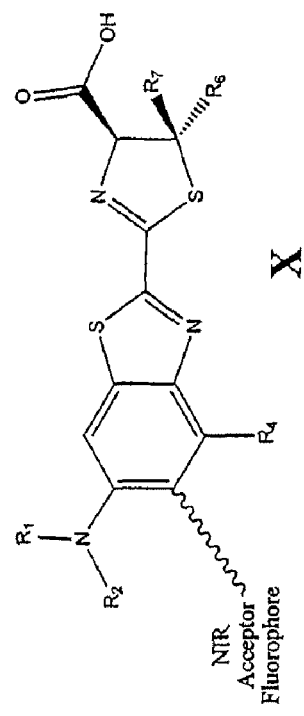

FIG. 4A shows a luciferin that includes a donor portion and an acceptor portion bonded to the amino group of the luciferin by a spacer (VIII), and a luciferin that includes a donor portion and an acceptor portion bonded to the aryl ring of the luciferin at the ortho position by a spacer (X).

In some embodiments, the spacer includes up to 24 carbon atoms. Optionally, the spacer can also include one or more N, O, P, S, F, Cl, Br, or I. For example, N can be part of an amino group, an amide group or an imine group. For example, O can be part of a hydroxyl group, a carboxylic acid group, an ester group, an anhydride group, an aldehyde group, a ketone group or a ether group. For example, S can be part of a thio-ester group, or a thiol group of a thio-ether group. For example, the 24 carbon atoms can be or can include a hydrocarbon fragment, e.g., an alkyl group, an alkenyl group, an alkynyl or an aryl group, or a hydrocarbon fragment that is substituted with one or more of N, O, S, F, Cl, Br, or I.

Figure 4B:
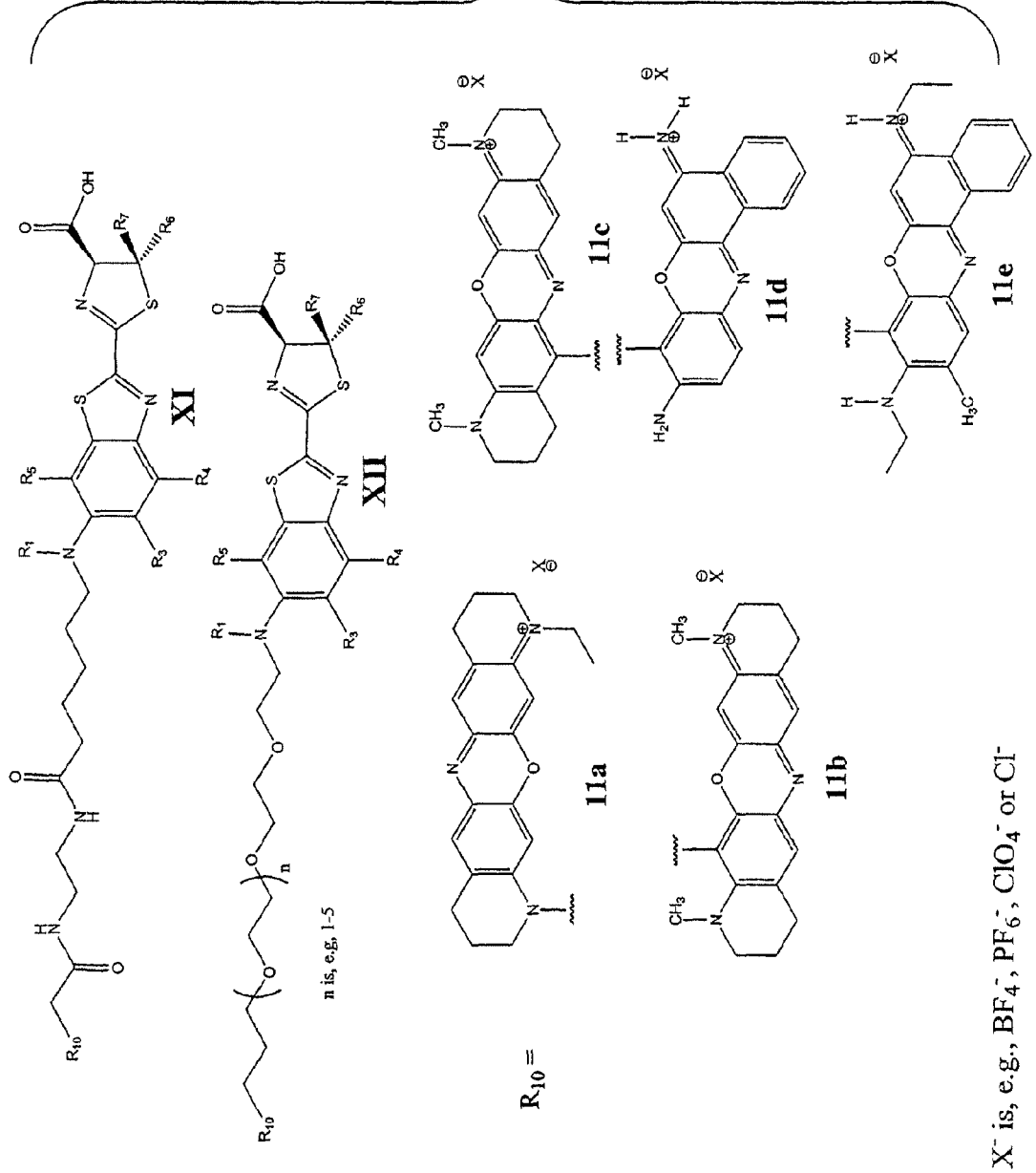
FIG. 4B is a series of generalized structures for novel amino luciferins, illustrating specific NIR fluorophores and spacers.

Referring now to FIG. 4B, in particular embodiments, the luciferin is represented by structure (XI). In such instances, the spacer can an C10 alkyl amide spacer, and the fluorophores can be any one of (11a), (11b), (11e), (11d) or (11e).

In some embodiments, the spacer is polymeric, e.g., a polymer fragment of a water-soluble polymer. For example, the spacer can be a polyethylene glycol (PEG) moiety or a PEG copolymer moiety, e.g., defined by —$(CH_2CH_2O)_n$—, in which n is an integer from 1 to 5.

Referring again to FIG. 4B, in particular embodiments, the luciferin is represented by structure (XII). In such instances, the spacer can be a PEG moiety in which n (see above) is between about 1 and 250. Just as was the case with Structure (XII), the fluorophores can be, e.g., are any one of (11a), (11b), (11e), (11d) or (11e) or others.

Figure 4C:
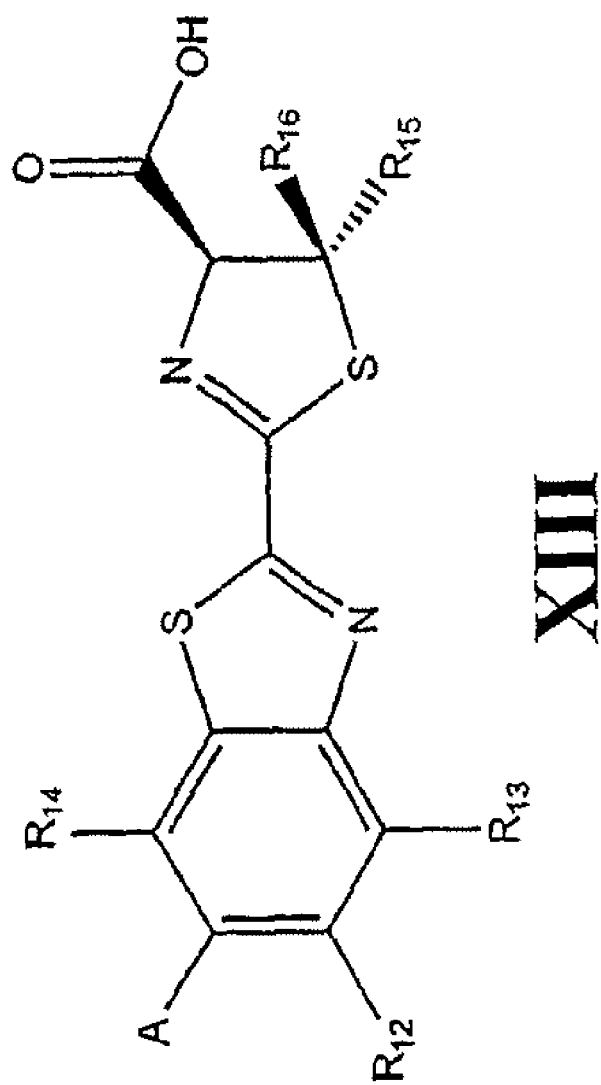
FIG. 4C is a generalized structure for some novel NIR fluorophore-substituted luciferins described herein.

Even other structures are possible. For example and by reference to FIG. 4C, other luciferins having dangling fluorophores can take the form of Structure (XIII). In such compounds of Structure (XIII), A is OH (which corresponds to a native firefly luciferin-type structure) or $NR_{10}R_{11}$, $R_{10}$ and $R_{11}$ each being independently H, or a third moiety that includes up to 12 carbon atoms. $R_{12}$ is a third moiety that includes a near infrared fluorophore, $R_{13}$ and $R_{14}$ are each independently H, OH, or a second moiety comprising up to 6 carbon atoms, and $R_{15}$ and $R_{16}$ are each independently H, or a second moiety that includes up to 8 carbon atoms. $R_{10}$, $R_{11}$, $R_{12}$, and $R_{14}$ together with one or more of its immediate neighbors may define one or more ring systems, each including up to 14 carbon atoms. The third moiety including up to 12 carbon atoms can be any of those moieties described above in reference to $R_1$ and $R_2$. The second moiety that includes up to 6 carbon atoms can be any of those moieties described above in reference to $R_4$ and $R_5$. The second moiety that includes up to 8 carbon atoms can be any of those moieties described above in reference to $R_6$ and $R_7$.

Fluorescent Proteins

When luciferins are covalently bonded in a pocket of a luciferase, fluorescent proteins are generated. In such instances, the luciferin chromophore can be protected from the chemical environment in which the fluorescent protein is placed.

Figure 5:
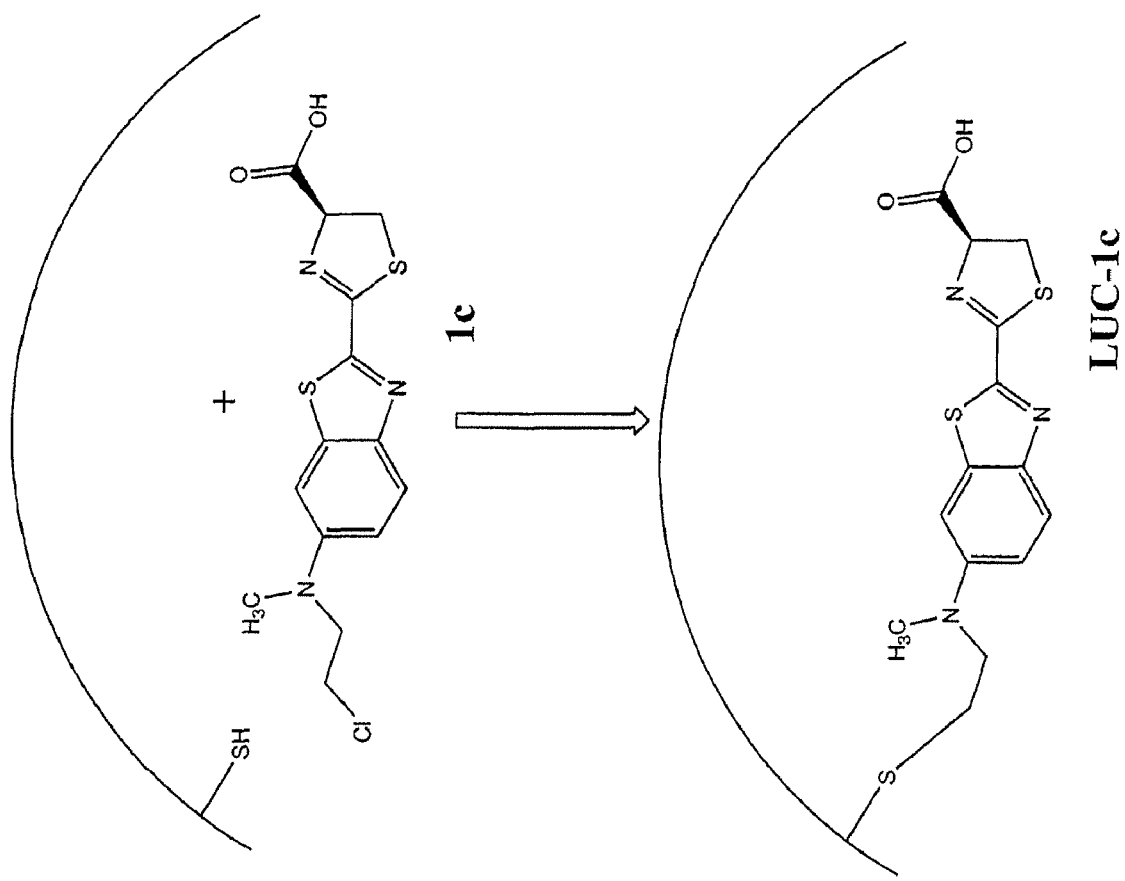
FIG. 5 is a schematic representation of a specific novel amino luciferin (1c) having a mustard group reacting with a thiol group in the pocket of (LUC).

Referring now to FIG. 5, the mustard compound (1c), or optionally the aziridine compound (2a) of FIG. 2C, can be covalently bonded in a luciferase pocket by reacting the compound (1c or 2a) with a luciferase having an exposed nucleophile, such as a thiol group or an amino group. FIG. 5 shows the mustard compound (1c) reacting with a thiol group in a pocket of a luciferase.

Mutated Luciferases

The red-shifted luciferins described herein may, in some cases, be too large to fit inside the binding pocket of a wild-type luciferase (for the crystal structure of a wild-type luciferase and several mutants see Nakatsu et al., *Nature* (2006) 440:372-376). In this case, the binding pocket of the luciferase can be mutated to enlarge the pocket to accommodate the red-shifted luciferin (for luciferase mutants see, e.g., Branchini et al., *Anal Biochem*, 2005, 345(1):140 and Branchini et al., *Biochem*. 42 (2003) 10429-36). For example, various amino acids can be altered, e.g., using standard site-directed mutagenesis methods, to amino acids with smaller side chains, thereby enlarging the binding pocket. For example, for substrate accommodation, amino acid residues corresponding to Arginine 218, Isoleucine 286, Serine 284, Serine 314, Alanine 313, Threonine 343 and/or Serine 347 of firefly luciferase can be altered. For example, for accessibility to solvent (e.g., fluorophore tethering), amino acid residues corresponding to Glutamate 311, Arginine 337 and/or Asparagine 229 of firefly luciferase can be altered. In general, conservative substitutions will be desirable. Mutated luciferases can be evaluated for activity using a standard luciferase assay, e.g., by contacting the mutated luciferase with a wild-type luciferin or a red-shifted luciferin as described herein, and detecting photons emitted therefrom.

For example, rational design methods can be used in which empirically determined or computationally generated models of a luciferin described herein and a luciferase binding site are evaluated, and mutations selected that optimize the fit of the luciferin in the binding site of the luciferase. Alternatively, a panel of binding site mutants of luciferase can be produced, and standard assays, e.g., high-throughput screening, can be used to identify optimal luciferin-mutant luciferase pairs for a particular application.

Methods of Use

The methods and compositions described herein can be used for in vivo imaging and may improve the speed, detection limit, and depth penetration of bioluminescence imaging. For example, the methods described herein can be used for the rapid and inexpensive evaluation of tumor progression and response to anti-cancer therapeutics in small animals, e.g., using transgenic non-human animals, e.g., mice, that express a luciferase reporter gene linked to a promoter or gene that is expressed, e.g., selectively expressed, in the cells that are desired to be imaged (Greer and Szalay, *Luminescence*, 2002, 17:43-74). In the same way, expression of a selected protein of interest can be imaged in real time in a living cell or animal, using a cell or transgenic animal that expresses a reporter construct including a nucleic acid encoding a luciferase linked in frame to a nucleic acid encoding the selected protein of interest, or to the promoter for the selected protein.

In general, the methods will be performed on cells or animals (e.g., non-human mammals, e.g., experimental animals, such as rodents, e.g., rats or mice) that express a luciferase or a mutated luciferase reporter construct. One of skill in the art will readily be able to make such cells or animals using standard molecular biological techniques. Sufficient amounts of any of the modified luciferins described herein are then added or administered to the cells or animals, and images of the NIR bioluminescence obtained using standard imaging methods. In this way, promoter activity, protein expression, protein subcellular localization, protein translocation, and protein half-life, can be evaluated in real time in living cells and animals.

When an experimental animal is used, the cells containing the NIR bioluminescence can be identified and excised, and evaluated further, e.g., using assays for gene expression, protein expression, or other genetic or biochemical parameters.

The design of specific luciferin/luciferase pairs (e.g., with different emission maxima) can allow for simultaneous imaging of bioluminescence from two or more luciferases.

Imaging Methods

The methods described herein can be practiced with any imaging system that can detect near infrared bioluminescence, e.g., the in vivo imaging systems described in Doyle et al., *Cellular Microbiology* (2004) 6(4):303-317. Common imaging systems are available from Xenogen (e.g., IVIS), Hamamatsu, Roper, and Kodak.

EXAMPLES

The disclosure is further described in the following examples, which do not limit its scope.

Example 1

Synthesis of Dimethylamino-Luciferin (1a)

This Example describes the synthesis of dimethylamino-luciferin (1a) (structure shown below).

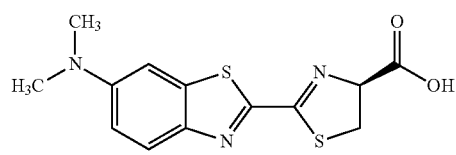

1a 6-amino-2-chlorobenzothiazole (29, FIG. 3D)

6-amino-2-chlorobenzothiazole (29) was synthesized following the procedure of White et al., 1966 (JACS 88, 2015).

2-chloro-6-dimethylaminobenzothiazole (40) (Shown Below)

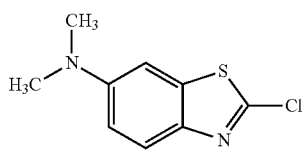

40

To a solution of (29) (0.1 mmol, 18.5 mg) in 1 ml dichloroethane was added 90 µl 37% formaldehyde, followed by 63.6 mg sodium triacetoxyborohydride, and 12 µl acetic acid. After 2 h, the solution was poured into water and extracted with ethyl acetate. The combined extracts were washed with water, dried over sodium sulfate, and the solvent removed by rotary evaporation. The crude material (21 mg) contained a small amount of monomethylated product, but was sufficiently pure to use directly in the next step. $^1$H-NMR (CDCl$_3$): d 7.75 (d, 1H, J=9.2 Hz), 6.95 (d, 1H, J=2.4 Hz), 6.90 (dd, 1H, J=2.4, 9.2 Hz), 3.02 (s, 6H).

2-cyano-6-dimethylaminobenzothiazole (44) (Shown Below)

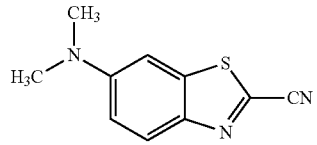

44

Potassium cyanide (18 mg) and (40) (18 mg) were dissolved in 1 ml DMSO and heated to 120° C. for 4 h. After cooling to room temperature, the reaction was poured into 0.2M potassium phosphate, pH 4.5. The aqueous layer was extracted with ethyl acetate three times, washed with water, and dried over sodium sulfate. The solvent was removed by rotary evaporation and the residue purified by silica gel chromatography (20% ethyl acetate in hexanes). $^1$H-NMR (d$_6$-DMSO): d 7.97 (d, 1H, J=9.2 Hz), 7.38 (d, 1H, J=2.4 Hz), 7.17 (dd, 1H, J=2.4, 9.2 Hz), 3.03 (s, 6H).

D-2-(6'-dimethylamino-2'-benzothiazolyl)-$\Delta^2$-thiazoline-4-carboxylic acid (1a)

D-cysteine-HCl (2.5 mg) was dissolved in 0.6 ml of deoxygenated 50 mM potassium phosphate buffer, pH 8.1 and added to 2 mg (10 µmol) of (44) in 0.6 ml of deoxygenated methanol and stirred under argon at room temperature. After 2 h, the methanol was removed by rotary evaporation, and the remaining aqueous solution was extracted with ethyl acetate twice and dried with sodium sulfate. Removal of the solvent by rotary evaporation yielded 3 mg of an orange-red solid. $^1$H-NMR (d$_6$-DMSO): d 7.89 (d, 1H, J=9.2 Hz), 7.29 (d, 1H, J=2.4 Hz), 7.05 (dd, 1H, J=2.4, 9.2 Hz), 5.35 (app t, 1H, X of ABX, J=8-10 Hz), 3.74-3.59 (m, 2H, AB of ABX), 3.01 (s, 6H).

Example 2

Synthesis of Monoethylamino-Luciferin 2-chloro-6-ethylaminobenzothiazole

To a solution of (29) (0.2 mmol, 36.8 mg) in 2 ml dichloroethane was added 0.2 mmol acetaldehyde, followed by 63.6 mg sodium triacetoxyborohydride, and 12 µl acetic acid. After 2 h, the solution was poured into water and extracted with ethyl acetate. The combined extracts were washed with water, dried over sodium sulfate, and the solvent removed by rotary evaporation.

2-cyano-6-ethylaminobenzothiazole

Potassium cyanide (18 mg) and 2-chloro-6-ethylaminobenzothiazole (18 mg) were dissolved in 1 ml DMSO and heated to 120° C. for 4 h. After cooling to room temperature, the reaction was poured into 0.2M potassium phosphate, pH 4.5. The aqueous layer was extracted with ethyl acetate three times, washed with water, and dried over sodium sulfate. The solvent was removed by rotary evaporation and the residue purified by silica gel chromatography (20% ethyl acetate in hexanes). $^1$H-NMR (d$_6$-DMSO): δ 7.85 (d, 1H, J=9.2 Hz), 7.13 (d, 1H, J=2.4 Hz), 6.98 (dd, 1H, J=2.4, 8.8 Hz), 6.44 (br t, 1H), 3.09 (m, 2H), 1.18 (t, 3H, J=7.2 Hz).

D-2-(6'-ethylamino-2'-benzothiazolyl)-Δ$^2$-thiazoline-4-carboxylic acid

D-cysteine-HCl (7 mg, 40 pimp was dissolved in 1 ml of deoxygenated 50 mM potassium phosphate buffer, pH 8 and added to 6.3 mg (31 μmol) of 2-cyano-6-ethylaminobenzothiazole in 1 ml of deoxygenated methanol and stirred under argon at room temperature. After 2 h, the solution was acidified to pH 5 with 0.1M HCl and the methanol was removed by rotary evaporation. The precipitated solid and the remaining aqueous solution was extracted with ethyl acetate three times and dried with sodium sulfate. Removal of the solvent by rotary evaporation yielded 8.8 mg of an orange-red solid. $^1$H-NMR (d$_6$-DMSO): δ 7.76 (d, 1H, J=8.8 Hz), 7.03 (s, 1H), 6.86 (d, 1H, J=9.2 Hz), 6.35 (m, 1H), 5.32 (app t, 1H, X of ABX), 3.75-3.55 (m, 2H, AB of ABX), 3.09 (m, 2H), 1.18 (t, 3H, J=7.2 Hz).

Example 3

Synthesis of Monoisopropylamino-Luciferin

2-chloro-6-isopropylaminobenzothiazole

To a solution of (29) (0.2 mmol, 36.8 mg) in 2 ml dichloroethane was added 0.2 mmol acetone (14.5 followed by 63.6 mg sodium triacetoxyborohydride, and 12 μl acetic acid. After 2 h, the solution was poured into water and extracted with ethyl acetate. The combined extracts were washed with water, dried over sodium sulfate, and the solvent removed by rotary evaporation.

2-cyano-6-isopropylaminobenzothiazole

Potassium cyanide (18 mg) and 2-chloro-6-isopropylaminobenzothiazole (18 mg) were dissolved in 1 ml DMSO and heated to 120° C. for 4 h. After cooling to room temperature, the reaction was poured into 0.2M potassium phosphate, pH 4.5. The aqueous layer was extracted with ethyl acetate three times, washed with water, and dried over sodium sulfate. The solvent was removed by rotary evaporation and the residue purified by silica gel chromatography (20% ethyl acetate in hexanes). $^1$H-NMR (d$_6$-DMSO): δ 7.83 (d, 1H, J=9.2 Hz), 7.15 (d, 1H, J=2.4 Hz), 6.97 (dd, 1H, J=2.4, 8.8 Hz), 6.52 (bd, 1H, J=7.2 Hz), 3.61 (m, 1H), 1.15 (d, 6H, J=6 Hz).

D-2-(6'-isopropylamino-2'-benzothiazolyl)-Δ$^2$-thiazoline-4-carboxylic acid D-cysteine-HCl (8.8 mg, 50 pimp was dissolved in 1.25 ml of deoxygenated 50 mM potassium phosphate buffer, pH 8 and added to 9.1 mg (42 μmol) of 2-cyano-6-isopropylaminobenzothiazole in 1.25 ml of deoxygenated methanol and stirred under argon at room temperature. After 2 h, the solution was acidified to pH 5 with 0.1M HCl and the methanol was removed by rotary evaporation. The precipitated solid and the remaining aqueous solution was extracted with ethyl acetate three times and dried with sodium sulfate. Removal of the solvent by rotary evaporation yielded 15 mg of an orange-red solid. $^1$H-NMR (d$_6$-DMSO): δ 7.75 (d, 1H, J=9.2 Hz), 7.05 (d, 1H, J=2.4 Hz), 6.85 (dd, 1H, J=2.4, 8.8 Hz), 6.22 (bd, 1H, J=7.2 Hz), 5.32 (app t, 1H, X of ABX, J=8-10 Hz), 3.61 (m, 1H), 3.55-3.72 (m, 2H, AB of ABX), 1.14 (d, 6H, J=6.4 Hz).

Example 4

Synthesis of Mono-N-Butylamino-Luciferin

2-chloro-6-butylaminobenzothiazole

To a solution of (29) (0.2 mmol, 36.8 mg) in 2 ml dichloroethane was added 0.2 mmol butyraldehyde (18 followed by 63.6 mg sodium triacetoxyborohydride, and 12 μl acetic acid. After 2 h, the solution was poured into water and extracted with ethyl acetate. The combined extracts were washed with water, dried over sodium sulfate, and the solvent removed by rotary evaporation, yielding 44.2 mg of a yellow solid. $^1$H-NMR (CDCl$_3$): δ 7.67 (d, 1H, J=9.2 Hz), 6.84 (d, 1H, J=2.4 Hz), 6.72 (dd, 1H, J=2.4, 9.2 Hz), 3.35 (bt, 1H), 3.15 (t, 2H), 1.65 (m, 2H), 1.45 (m, 2H), 0.97 (t, 3H, J=7.6 Hz).

2-cyano-6-butylaminobenzothiazole

Potassium cyanide (18 mg) and 2-chloro-6-butylaminobenzothiazole (18 mg) were dissolved in 1 ml DMSO and heated to 120° C. for 4 h. After cooling to room temperature, the reaction was poured into 0.2M potassium phosphate, pH 4.5. The aqueous layer was extracted with ethyl acetate three times, washed with water, and dried over sodium sulfate. The solvent was removed by rotary evaporation and the residue purified by silica gel chromatography (20% ethyl acetate in hexanes). $^1$H-NMR (d$_6$-DMSO): δ 7.84 (d, 1H, J=8.8 Hz), 7.14 (d, 1H, J=2.4 Hz), 6.99 (dd, 1H, J=2.4, 9.2 Hz), 6.67 (br t, 1H), 3.06 (m, 2H), 1.55 (m, 2H), 1.39 (m, 2H), 0.90 (t, 3H, J=7.4 Hz).

D-2-(6'-butylamino-2'-benzothiazolyl)-Δ$^2$-thiazoline-4-carboxylic acid

D-cysteine-HCl (7 mg, 40 mmol) was dissolved in 1 ml of deoxygenated 50 mM potassium phosphate buffer, pH 8 and added to 6.6 mg (29 mmol) of 2-cyano-6-butylaminobenzothiazole in 1 ml of deoxygenated methanol and stirred under argon at room temperature. After 2 h, the solution was acidified to pH 5 with 0.1M HCl and the methanol was removed by rotary evaporation. The precipitated solid and the remaining aqueous solution was extracted with ethyl acetate three times and dried with sodium sulfate. Removal of the solvent by rotary evaporation yielded 8.5 mg of an orange-red solid. $^1$H-NMR (d$_6$-DMSO): δ 7.75 (d, 1H, J=9.2 Hz), 7.03 (s, 1H), 6.87 (d, 1H, J=9.2 Hz), 6.36 (m, 1H), 5.32 (app t, 1H, X of ABX), 3.75-3.55 (m, 2H, AB of ABX), 3.04 (m, 2H), 1.54 (m, 2H), 1.37 (m, 2H), 0.90 (t, 3H, J=7.2 Hz).

Example 5

Luciferase Assay

Firefly luciferase (from Promega's pGL2-Basic vector (X65323), or pGL3-Basic vector (U47295)) was cloned into pGEX-6P-1 and expressed as a GST fusion protein in *E. coli*. The GST tag was removed by cleavage with PreScission™ protease, providing a composition of substantially purified luciferase. The emission spectrum of luciferase at pH 7.8 was recorded in a Spex Fluoromax™-3. The maximal emission in the presence of the native substrate D-luciferin was 555 nm.

With amino-luciferin as substrate, the emission shifted to 593 nm (White et al., *JACS* (1966) 88: 2015 reported 605 nm). The monoalkylaminoluciferins (ethylamino, isopropylamino, and n-butylamino) all shifted emission to 607 nm. When dimethylamino-luciferin (1a) was used as a substrate, the emission was bathochromatically shifted to 624 nm.

OTHER EMBODIMENTS

A number of embodiments have been described. Nevertheless, it will be understood that various modifications may be made without departing from the spirit and scope of the invention. Other embodiments are within the scope of the following claims.

What I claim is:
1. A method of imaging a sample, the method comprising:
obtaining a sample comprising a luciferase;
contacting the sample with a compound of Structure (III) or (IV), or a salt or acid ester thereof:

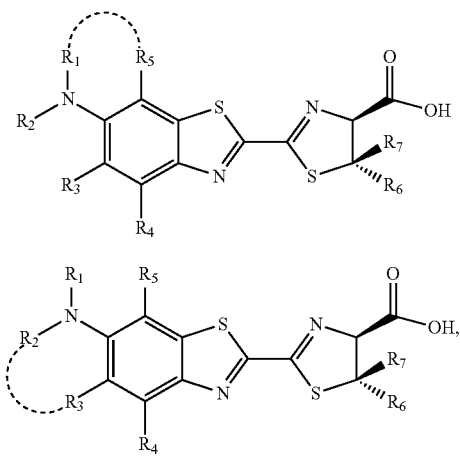

wherein:
$R_1$ and $R_2$ are each independently H, $C_{1-12}$ alkyl optionally substituted by an amino group, an amide group, an imine group, a hydroxyl group, a carboxylic acid group, an ester group, an anhydride group, an aldehyde group, a ketone group, an ether group, a thio-ester group, a thiol group, a thioether group, a phosphate group, a phosphonate group, a phosphine group, a phosphoramide group, an alkyl group, an alkenyl group, an alkynyl group, an aryl group, F, Cl, Br, I, or a near infrared fluorophore, optionally with a spacer, provided that $R_1$ and $R_2$ are not both H;
$R_3$ is H, OH, $C_{1-12}$ alkyl optionally substituted by an amino group, an amide group, an imine group, a hydroxyl group, a carboxylic acid group, an ester group, an anhydride group, an aldehyde group, a ketone group, an ether group, a thio-ester group, a thiol group, a thioether group, a phosphate group, a phosphonate group, a phosphine group, a phosphoramide group, an alkyl group, an alkenyl group, an alkynyl group, an aryl group, F, Cl, Br, I, or a near infrared fluorophore, optionally with a spacer;
$R_4$ and $R_5$ are each independently H, OH, or $C_{1-6}$ alkyl optionally substituted by an amino group, an amide group, an imine group, a hydroxyl group, a carboxylic acid group, an ester group, an anhydride group, an aldehyde group, a ketone group, an ether group, a thio-ester group, a thiol group, a thioether group, a phosphate group, a phosphonate group, a phosphine group, a phosphoramide group, an alkyl group, an alkenyl group, an alkynyl group, an aryl group, F, Cl, Br, or I;
$R_6$ and $R_7$ are each independently H, or $C_{1-8}$ alkyl optionally substituted by an amino group, an amide group, an imine group, a hydroxyl group, a carboxylic acid group, an ester group, an anhydride group, an aldehyde group, a ketone group, an ether group, a thio-ester group, a thiol group, a thioether group, a phosphate group, a phosphonate group, a phosphine group, a phosphoramide group, an alkyl group, an alkenyl group, an alkynyl group, an aryl group, F, Cl, Br, or I;
$R_1$, $R_2$, $R_3$, or $R_5$ together with one or more of its immediate neighbors define one or more 5, 6, or 7-membered rings; wherein
the rings optionally include one or more groups selected from: an amino group, an amide group, an imine group, a hydroxyl group, a carboxylic acid group, an ester group, an anhydride group, an aldehyde group, a ketone group, an ether group, a thio-ester group, a thiol group, a thioether group, a phosphate group, a phosphonate group, a phosphine group, a phosphoramide group, an alkyl group, an alkenyl group, an alkynyl group, an aryl group, F, Cl, Br, and I; and
the spacer is $C_{1-24}$ alkyl optionally substituted by one or more groups selected from: an amino group, an amide group, an imine group, a hydroxyl group, a carboxylic acid group, an ester group, an anhydride group, an aldehyde group, a ketone group, an ether group, a thio-ester group, a thiol group, a thioether group, a phosphate group, a phosphonate group, a phosphine group, a phosphoramide group, an alkyl group, an alkenyl group, an alkynyl group, an aryl group, F, Cl, Br, and I; and
detecting bioluminescent emission from the sample.
2. The method of claim 1, wherein the spacer is a polymer fragment of a water-soluble polymer fragment.
3. The method of claim 1, wherein $R_3$, $R_4$, $R_5$, $R_6$ and $R_7$ are each hydrogen, or an alkyl group having fewer than 4 carbon atoms.
4. A method of imaging a sample, the method comprising:
obtaining a sample comprising a luciferase;
contacting the sample with a compound of Structure (V), or salts or acid esters thereof:

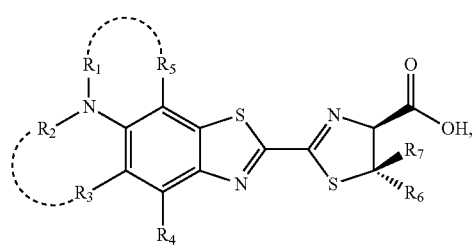

wherein
$R_4$ is H, OH, or $C_{1-6}$ alkyl optionally substituted by an amino group, an amide group, an imine group, a hydroxyl group, a carboxylic acid group, an ester group, an anhydride group, an aldehyde group, a ketone group, an ether group, a thio-ester group, a thiol group, a thioether group, a phosphate group, a phosphonate group, a phosphine group, a phosphoramide group, an alkyl group, an alkenyl group, an alkynyl group, an aryl group, F, Cl, Br, or I;

$R_6$ and $R_7$ are each independently H or $C_{1-8}$ alkyl optionally substituted by an amino group, an amide group, an imine group, a hydroxyl group, a carboxylic acid group, an ester group, an anhydride group, an aldehyde group, a ketone group, an ether group, a thio-ester group, a thiol group, a thioether group, a phosphate group, a phosphonate group, a phosphine group, a phosphoramide group, an alkyl group, an alkenyl group, an alkynyl group, an aryl group, F, Cl, Br, or I;

$R_1$ and $R_5$ and $R_2$ and $R_3$ together with one or more of its immediate neighbors define one or more 5, 6, or 7-membered rings; and wherein the rings optionally include one or more groups selected from: an amino group, an amide group, an imine group, a hydroxyl group, a carboxylic acid group, an ester group, an anhydride group, an aldehyde group, a ketone group, an ether group, a thio-ester group, a thiol group, a thioether group, a phosphate group, a phosphonate group, a phosphine group, a phosphoramide group, an alkyl group, an alkenyl group, an alkynyl group, an aryl group, F, Cl, Br, and I; and, detecting bioluminescent emission from the sample.

5. The method of claim 1, wherein $R_1$ and/or $R_2$ are each $C_{1-12}$ alkyl linked to a near infrared fluorophore.

6. The method of claim 1, wherein $R_3$ is $C_{1-12}$ alkyl linked to a near infrared fluorophore.

7. The method of claim 1, wherein the compounds are selected from:

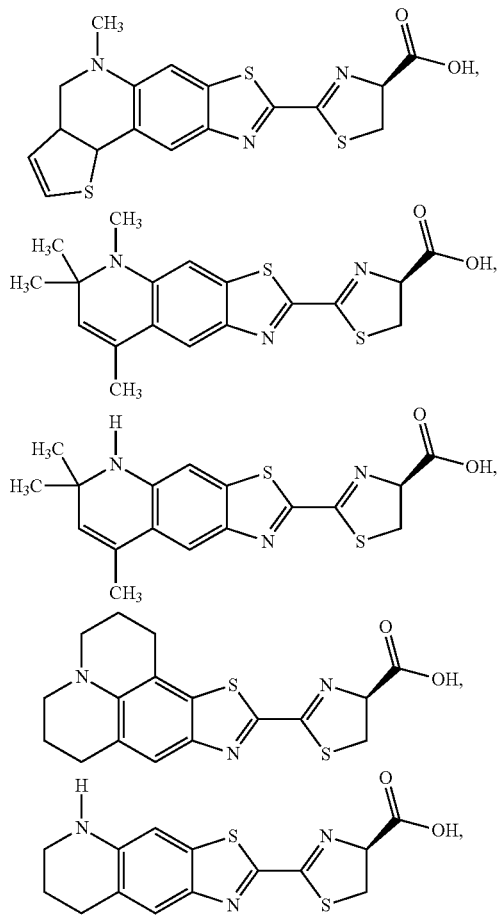

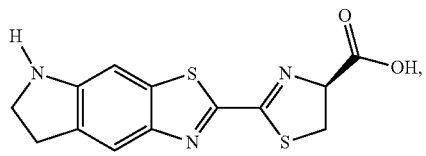

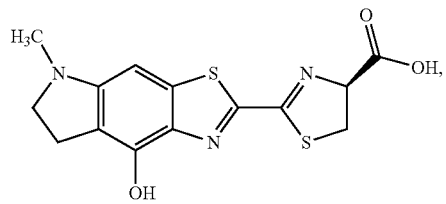

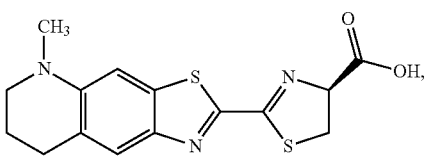

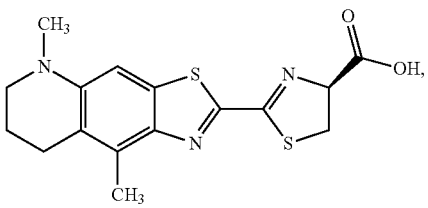

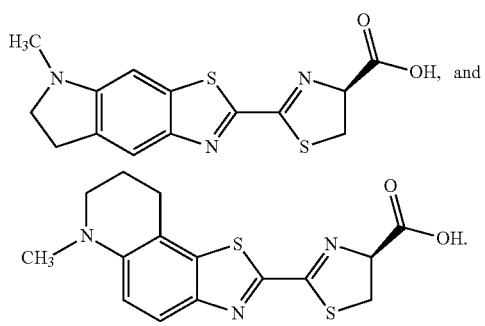

8. The method of claim 1, wherein the luciferase has a mutation at Serine 347 to an amino acid with a smaller side chain.

9. The method of claim 8, wherein the luciferase has a mutation at Serine 347 to alanine

10. The method of claim 4, wherein the sample comprises a cell lysate.

11. The method of claim 4, further comprising providing a plurality of samples, and detecting emissions from each of the samples.

12. A method of imaging an animal, the method comprising:

obtaining an animal having at least one cell expressing a luciferase;

administering to the animal a compound of Structure (V), or salts or acid esters thereof:

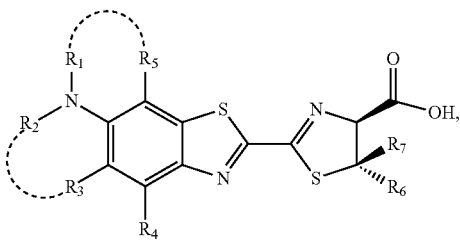

wherein
R₄ is H, OH, or $C_{1-6}$ alkyl optionally substituted by an amino group, an amide group, an imine group, a hydroxyl group, a carboxylic acid group, an ester group, an anhydride group, an aldehyde group, a ketone group, an ether group, a thio-ester group, a thiol group, a thio-ether group, a phosphate group, a phosphonate group, a phosphine group, a phosphoramide group, an alkyl group, an alkenyl group, an alkynyl group, an aryl group, F, Cl, Br, or I;

$R_6$ and $R_7$ are each independently H or $C_{1-8}$ alkyl optionally substituted by an amino group, an amide group, an imine group, a hydroxyl group, a carboxylic acid group, an ester group, an anhydride group, an aldehyde group, a ketone group, an ether group, a thio-ester group, a thiol group, a thioether group, a phosphate group, a phosphonate group, a phosphine group, a phosphoramide group, an alkyl group, an alkenyl group, an alkynyl group, an aryl group, F, Cl, Br, or I;

$R_1$ and $R_5$ and $R_2$ and $R_3$ together with one or more of its immediate neighbors define one or more 5, 6, or 7-membered rings; and wherein the rings optionally include one or more groups selected from: an amino group, an amide group, an imine group, a hydroxyl group, a carboxylic acid group, an ester group, an anhydride group, an aldehyde group, a ketone group, an ether group, a thio-ester group, a thiol group, a thioether group, a phosphate group, a phosphonate group, a phosphine group, a phosphoramide group, an alkyl group, an alkenyl group, an alkynyl group, an aryl group, F, Cl, Br, and I; and, detecting emission from the compound to image the animal.

13. A method of imaging a cell, the method comprising:
obtaining a cell expressing a luciferase;
contacting the cell with a compound of Structure (V), or salts or acid esters thereof:

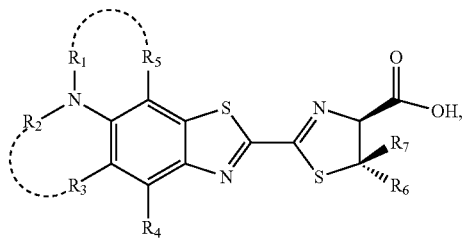

wherein
$R_4$ is H, OH, or $C_{1-6}$ alkyl optionally substituted by an amino group, an amide group, an imine group, a hydroxyl group, a carboxylic acid group, an ester group, an anhydride group, an aldehyde group, a ketone group, an ether group, a thio-ester group, a thiol group, a thio-ether group, a phosphate group, a phosphonate group, a phosphine group, a phosphoramide group, an alkyl group, an alkenyl group, an alkynyl group, an aryl group, F, Cl, Br, or I;

$R_6$ and $R_7$ are each independently H or $C_{1-8}$ alkyl optionally substituted by an amino group, an amide group, an imine group, a hydroxyl group, a carboxylic acid group, an ester group, an anhydride group, an aldehyde group, a ketone group, an ether group, a thio-ester group, a thiol group, a thioether group, a phosphate group, a phosphonate group, a phosphine group, a phosphoramide group, an alkyl group, an alkenyl group, an alkynyl group, an aryl group, F, Cl, Br, or I;

$R_1$ and $R_5$ and $R_2$ and $R_3$ together with one or more of its immediate neighbors define one or more 5, 6, or 7-membered rings; and wherein the rings optionally include one or more groups selected from: an amino group, an amide group, an imine group, a hydroxyl group, a carboxylic acid group, an ester group, an anhydride group, an aldehyde group, a ketone group, an ether group, a thio-ester group, a thiol group, a thioether group, a phosphate group, a phosphonate group, a phosphine group, a phosphoramide group, an alkyl group, an alkenyl group, an alkynyl group, an aryl group, F, Cl, Br, and I; and, detecting emission from the compound to image the cell.

14. The method of claim 13, wherein the luciferase is expressed from a reporter construct.

15. The method of claim 14, wherein the reporter construct comprises a nucleic acid encoding a luciferase operably linked to a selected promoter, and detecting emission from the luciferin provides an indication of promoter activity.

16. The method of claim 14, wherein the reporter construct comprises a nucleic acid encoding a luciferase linked in frame to a nucleic acid encoding a selected protein, and detecting emission from the luciferin provides an indication of one or more of expression, subcellular localization, translocation, and half-life of the protein.

* * * * *

UNITED STATES PATENT AND TRADEMARK OFFICE
CERTIFICATE OF CORRECTION

PATENT NO. : 8,216,550 B2  Page 1 of 1
APPLICATION NO. : 13/027233
DATED : July 10, 2012
INVENTOR(S) : Stephen C. Miller It is certified that error appears in the above-identified patent and that said Letters Patent is hereby corrected as shown below:

On page 7, in Col. 18, line 54, In Claim 9, after "alanine" insert --.--.

Signed and Sealed this
Ninth Day of October, 2012

David J. Kappos
*Director of the United States Patent and Trademark Office*